(12) United States Patent
Utterberg et al.

(10) Patent No.: US 8,377,039 B2
(45) Date of Patent: *Feb. 19, 2013

(54) INJECTION SITE FOR MALE LUER OR OTHER TUBULAR CONNECTOR

(75) Inventors: David S. Utterberg, Seattle, WA (US); William J. Schnell, Libertyville, IL (US); David Bell, Grayslake, IL (US)

(73) Assignee: NxStage Medical, Inc., Lawrence, MA (US)

( * ) Notice: Subject to any disclaimer, the term of this patent is extended or adjusted under 35 U.S.C. 154(b) by 2167 days.

This patent is subject to a terminal disclaimer.

(21) Appl. No.: 10/423,484

(22) Filed: Apr. 25, 2003

(65) Prior Publication Data

US 2004/0068239 A1    Apr. 8, 2004

Related U.S. Application Data

(63) Continuation-in-part of application No. 10/264,863, filed on Oct. 4, 2002, now Pat. No. 7,025,744.

(51) Int. Cl.
    *A61M 25/16*    (2006.01)
(52) U.S. Cl. .................................................. 604/533
(58) Field of Classification Search .......... 604/534–539, 604/905, 83, 256, 533, 167.03, 167.04; 251/149.1; 137/845
    See application file for complete search history.

(56) References Cited

U.S. PATENT DOCUMENTS

| | | |
|---|---|---|
| 3,974,832 A | 8/1976 | Kruck |
| 3,977,400 A | 8/1976 | Moorehead |
| 3,977,403 A | 8/1976 | Patel |
| 3,994,293 A | 11/1976 | Ferro |
| 3,994,294 A | 11/1976 | Knute |
| 4,000,739 A | 1/1977 | Stevens |
| 4,019,512 A | 4/1977 | Tenczar |
| 4,063,555 A | 12/1977 | Ulinder |
| 4,076,285 A | 2/1978 | Martinez |
| 4,080,965 A | 3/1978 | Phillips |
| 4,105,187 A | 8/1978 | Huber |
| 4,106,491 A | 8/1978 | Guerra |
| 4,121,585 A | 10/1978 | Becker, Jr. |

(Continued)

FOREIGN PATENT DOCUMENTS

| | | |
|---|---|---|
| CA | 1 248 832 | 1/1989 |
| DE | 33 03 718 C1 | 10/1984 |

(Continued)

OTHER PUBLICATIONS

Publication from ERCI: "Sharps Safety and Needle Stick Prevention"; pp. 95-108 (2001).

(Continued)

*Primary Examiner* — Christopher D Koharski
(74) *Attorney, Agent, or Firm* — Miles & Stockbridge P.C.; Mark A. Catan

(57) ABSTRACT

A medical device has an interior for containment of fluids; an opening into the interior, an elastomeric wall comprising a fixedly placed, flexible barrier across the opening; and a retention wall positioned adjacent to a peripheral portion of the elastomeric wall. The retention wall defines a central opening and has a generally rigid retention zone surrounding the central opening, to engage and retain a connector tube which is advanced into the central opening to open a flow aperture through the elastomeric wall, for flow through the wall and connector tube. One of the retention zone and connector tube may be made of a material of sufficient hardness that material of the other engaging member is deformed by engagement therewith, which increases the strength of retention between the retention wall and the connector tube.

44 Claims, 12 Drawing Sheets

U.S. PATENT DOCUMENTS

| | | |
|---|---|---|
| 4,128,098 A | 12/1978 | Bloom et al. |
| 4,143,853 A * | 3/1979 | Abramson ................. 251/149.1 |
| 4,149,535 A | 4/1979 | Volder |
| 4,161,949 A | 7/1979 | Thanawalla |
| 4,177,814 A | 12/1979 | Knepshield et al. |
| 4,197,848 A | 4/1980 | Garrett et al. |
| 4,200,096 A | 4/1980 | Charvin |
| 4,201,208 A | 5/1980 | Cambio, Jr. |
| 4,219,912 A | 9/1980 | Adams |
| 4,240,411 A | 12/1980 | Hosono |
| 4,261,357 A | 4/1981 | Kontos |
| 4,324,239 A | 4/1982 | Gordon et al. |
| 4,326,569 A | 4/1982 | Vaillancourt |
| 4,334,551 A | 6/1982 | Pfister |
| 4,338,933 A | 7/1982 | Bayard et al. |
| 4,387,879 A * | 6/1983 | Tauschinski ............... 251/149.1 |
| 4,429,856 A | 2/1984 | Jackson |
| 4,436,519 A | 3/1984 | O'Neill |
| 4,443,219 A | 4/1984 | Meisch et al. |
| 4,475,548 A | 10/1984 | Muto |
| 4,508,367 A | 4/1985 | Oreopoulos et al. |
| 4,511,359 A | 4/1985 | Vaillancourt |
| 4,512,766 A | 4/1985 | Vailancourt |
| 4,535,820 A | 8/1985 | Raines |
| 4,559,043 A | 12/1985 | Whitehouse et al. |
| 4,601,703 A | 7/1986 | Herlitze |
| 4,610,469 A | 9/1986 | Wolff-Mooij |
| 4,610,665 A | 9/1986 | Matsumoto et al. |
| 4,610,674 A | 9/1986 | Suzuki et al. |
| 4,614,267 A | 9/1986 | Larkin |
| 4,629,450 A | 12/1986 | Suzuki et al. |
| 4,645,494 A | 2/1987 | Lee et al. |
| 4,649,904 A | 3/1987 | Krauter et al. |
| 4,655,752 A | 4/1987 | Honkanen et al. |
| 4,666,429 A | 5/1987 | Stone |
| 4,673,393 A | 6/1987 | Suzuki et al. |
| 4,673,400 A | 6/1987 | Martin |
| 4,683,916 A | 8/1987 | Raines |
| 4,745,950 A | 5/1988 | Mathieu |
| 4,752,287 A | 6/1988 | Kurtz et al. |
| 4,752,292 A | 6/1988 | Lopez et al. |
| 4,758,225 A | 7/1988 | Cox et al. |
| 4,765,588 A | 8/1988 | Atkinson |
| 4,768,568 A | 9/1988 | Fournier et al. |
| 4,769,017 A | 9/1988 | Fath et al. |
| 4,786,281 A | 11/1988 | Valentini et al. |
| 4,798,594 A | 1/1989 | Hillstead |
| 4,809,679 A | 3/1989 | Shimonaka et al. |
| 4,823,833 A | 4/1989 | Hogan et al. |
| 4,842,591 A | 6/1989 | Luther |
| 4,871,356 A | 10/1989 | Haindl et al. |
| 4,874,377 A | 10/1989 | Newgard et al. |
| 4,874,378 A | 10/1989 | Hillstead |
| 4,895,346 A | 1/1990 | Steigerwald |
| 4,909,798 A | 3/1990 | Fleischhacker et al. |
| 4,917,668 A | 4/1990 | Haindl |
| 4,929,235 A | 5/1990 | Merry et al. |
| 4,935,010 A | 6/1990 | Cox et al. |
| 4,950,260 A | 8/1990 | Bonaldo |
| 4,954,149 A | 9/1990 | Fullemann |
| 4,960,412 A | 10/1990 | Fink |
| 4,981,469 A | 1/1991 | Whitehouse et al. |
| 4,984,829 A | 1/1991 | Saigo et al. |
| 5,000,745 A | 3/1991 | Guest et al. |
| 5,006,114 A | 4/1991 | Rogers et al. |
| 5,009,391 A | 4/1991 | Steigerwald |
| 5,041,097 A | 8/1991 | Johnson |
| 5,060,812 A | 10/1991 | Ogle, II |
| 5,061,253 A | 10/1991 | Yoshida |
| 5,064,416 A | 11/1991 | Newgard et al. |
| 5,080,654 A | 1/1992 | Picha et al. |
| 5,092,857 A | 3/1992 | Fleischhacker |
| 5,100,394 A | 3/1992 | Dudar et al. |
| 5,104,379 A | 4/1992 | Nakamura et al. |
| 5,108,380 A | 4/1992 | Herlitze et al. |
| 5,114,408 A | 5/1992 | Fleischhaker et al. |
| 5,127,904 A | 7/1992 | Loo et al. |
| 5,135,489 A | 8/1992 | Jepson et al. |
| 5,147,333 A | 9/1992 | Raines |
| 5,158,554 A | 10/1992 | Jepson et al. |
| 5,167,637 A | 12/1992 | Okada et al. |
| 5,167,648 A | 12/1992 | Jepson et al. |
| 5,171,234 A | 12/1992 | Jepson et al. |
| 5,178,607 A | 1/1993 | Lynn et al. |
| 5,184,652 A | 2/1993 | Fan |
| 5,188,620 A | 2/1993 | Jepson et al. |
| 5,195,980 A | 3/1993 | Catlin |
| 5,199,948 A | 4/1993 | McPhee |
| 5,201,725 A | 4/1993 | Kling |
| 5,203,775 A | 4/1993 | Frank et al. |
| 5,211,634 A | 5/1993 | Vaillancourt |
| 5,211,638 A | 5/1993 | Dudar et al. |
| 5,215,537 A | 6/1993 | Lynn et al. |
| 5,215,538 A * | 6/1993 | Larkin ........................ 604/249 |
| 5,242,393 A | 9/1993 | Brimhall et al. |
| 5,242,432 A | 9/1993 | DeFrank |
| 5,250,033 A | 10/1993 | Evans et al. |
| 5,251,873 A | 10/1993 | Atkinson et al. |
| 5,269,771 A | 12/1993 | Thomas et al. |
| 5,279,571 A | 1/1994 | Larkin |
| 5,295,657 A | 3/1994 | Atkinson |
| 5,295,658 A | 3/1994 | Atkinson et al. |
| 5,328,041 A | 7/1994 | Hook et al. |
| 5,336,192 A | 8/1994 | Palestrant |
| 5,342,316 A * | 8/1994 | Wallace ................... 604/167.02 |
| 5,360,413 A | 11/1994 | Leason et al. |
| 5,368,801 A | 11/1994 | Vaillancourt |
| 5,380,306 A | 1/1995 | Brinon |
| 5,402,982 A | 4/1995 | Atkinson et al. |
| 5,409,125 A | 4/1995 | Kimber et al. |
| 5,417,673 A | 5/1995 | Gordon |
| 5,439,451 A | 8/1995 | Collinson et al. |
| 5,441,487 A | 8/1995 | Vedder |
| 5,445,630 A | 8/1995 | Richmond |
| 5,453,097 A | 9/1995 | Paradis |
| 5,456,675 A | 10/1995 | Wolbring et al. |
| 5,465,938 A | 11/1995 | Werge et al. |
| 5,466,219 A | 11/1995 | Lynn et al. |
| 5,470,319 A | 11/1995 | Mayer |
| 5,474,544 A | 12/1995 | Lynn |
| 5,501,426 A | 3/1996 | Atkinson et al. |
| 5,522,804 A | 6/1996 | Lynn |
| 5,533,708 A | 7/1996 | Atkinson et al. |
| 5,533,983 A | 7/1996 | Haining |
| 5,540,661 A | 7/1996 | Tomisaka et al. |
| 5,549,651 A | 8/1996 | Lynn |
| 5,578,059 A | 11/1996 | Patzer |
| 5,584,808 A | 12/1996 | Healy |
| 5,620,434 A | 4/1997 | Brony et al. |
| 5,674,206 A | 10/1997 | Allton et al. |
| 5,685,866 A | 11/1997 | Lopez |
| 5,697,915 A | 12/1997 | Lynn |
| 5,702,019 A * | 12/1997 | Grimard ........................ 215/301 |
| RE35,841 E | 7/1998 | Frank et al. |
| 5,797,897 A | 8/1998 | Jepson et al. |
| 5,871,500 A | 2/1999 | Jepson et al. |
| 5,899,888 A | 5/1999 | Jepson et al. |
| 5,921,419 A | 7/1999 | Niedospial et al. |
| 5,957,898 A | 9/1999 | Jepson et al. |
| 5,971,181 A | 10/1999 | Niedospial, Jr. et al. |
| 6,036,171 A | 3/2000 | Weinheimer et al. |
| 6,039,302 A | 3/2000 | Cote, Sr. et al. |
| 6,039,718 A | 3/2000 | Niedospial, Jr. |
| 6,048,335 A | 4/2000 | Mayer |
| 6,089,541 A | 7/2000 | Weinheimer et al. |
| 6,123,690 A | 9/2000 | Mejslov |
| 6,152,900 A | 11/2000 | Mayer |
| 6,162,206 A | 12/2000 | Bindokas et al. |
| 6,171,287 B1 | 1/2001 | Lynn |
| 6,193,697 B1 | 2/2001 | Jepson et al. |
| 6,206,861 B1 | 3/2001 | Mayer |
| 6,213,996 B1 | 4/2001 | Jepson et al. |
| 6,245,048 B1 | 6/2001 | Fangrow, Jr. et al. |
| 6,261,266 B1 | 7/2001 | Jepson et al. |
| 6,261,282 B1 | 7/2001 | Jepson et al. |
| 6,290,206 B1 | 9/2001 | Doyle |
| 6,344,033 B1 | 2/2002 | Jepson et al. |

| | | | |
|---|---|---|---|
| 6,416,499 B2 | 7/2002 | Paul | |
| 6,419,825 B1 | 7/2002 | Hahmann et al. | |
| 7,025,744 B2 | 4/2006 | Utterberg et al. | |
| 7,056,308 B2 | 6/2006 | Utterberg | |
| 7,569,047 B2 | 8/2009 | Utterberg | |
| 2002/0002351 A1 | 1/2002 | Cote et al. | |

FOREIGN PATENT DOCUMENTS

| | | |
|---|---|---|
| DE | 3627978 | 6/1987 |
| DE | 19546580 | 12/1996 |
| EP | 0472088 | 2/1992 |
| EP | 0674914 | 10/1995 |
| EP | 1190735 A | 3/2002 |
| EP | 1 217 284 A1 | 6/2002 |
| EP | 1211184 | 6/2002 |
| EP | 1243285 | 9/2002 |
| WO | WO 91/05581 | 5/1991 |
| WO | 95/03841 | 2/1995 |
| WO | WO 02/04065 A2 | 1/2002 |
| WO | WO 02/34326 | 5/2002 |

OTHER PUBLICATIONS

Photograph of JMS Connector with Planecta—Japanese Catalog Page.
Drawing labeled Fresenius Connector.
European Search Report (dated Sep. 29, 2006; 6 pgs.).
Supplementary European Search Report issued May 20, 2010, in European Patent Application No. 04777299.
Office Action issued Mar. 9, 2011, in European Patent Application No. 04777299.

* cited by examiner

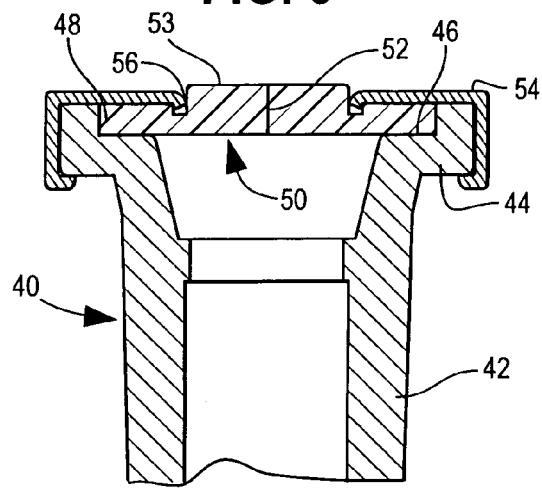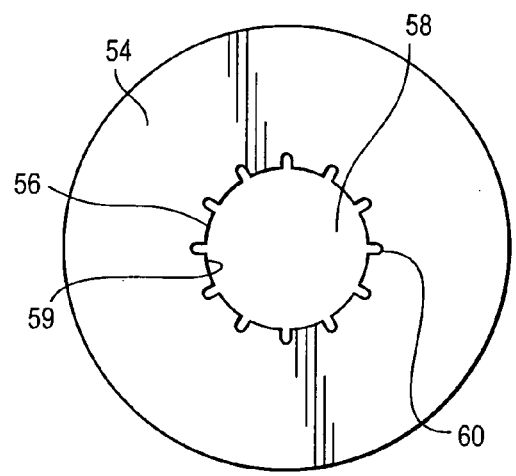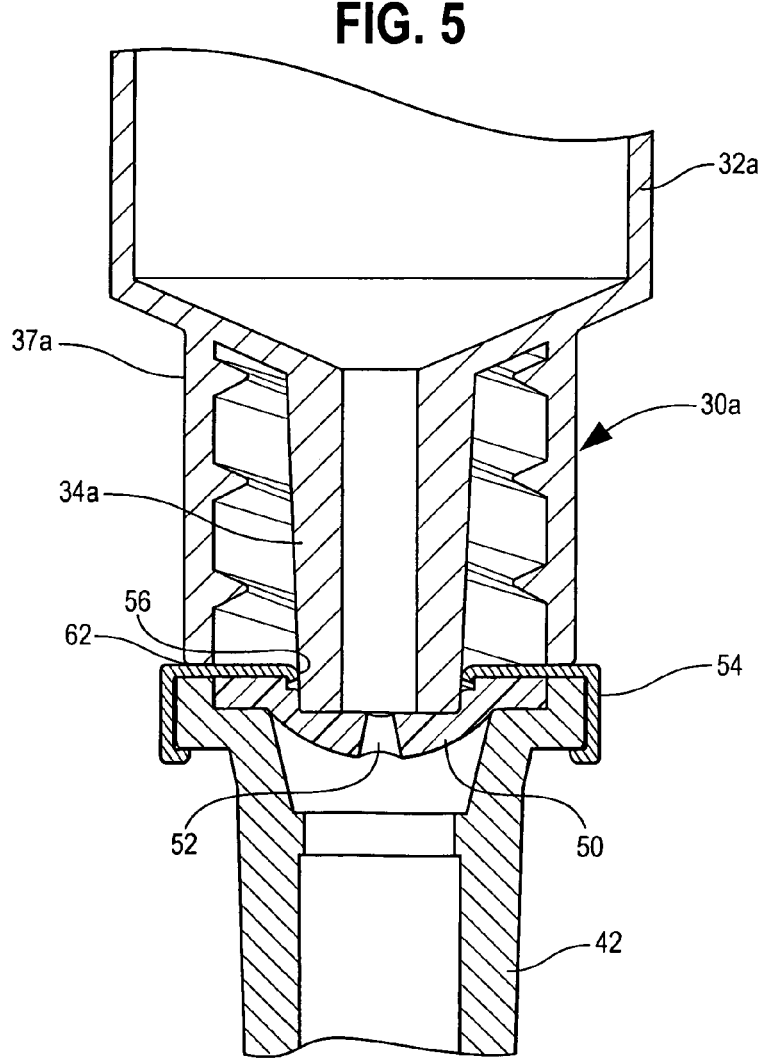

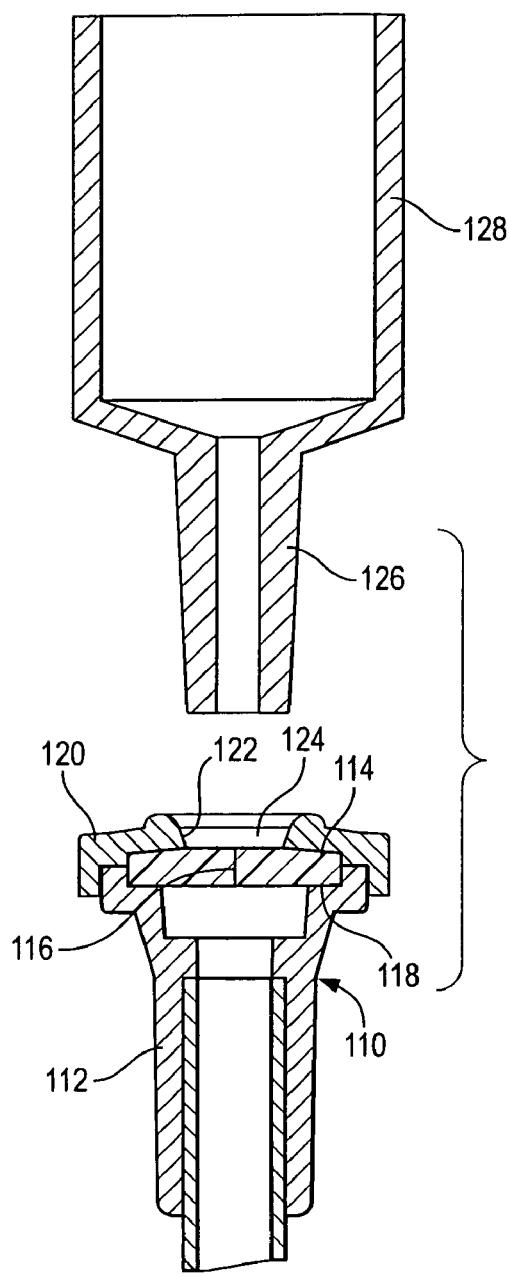
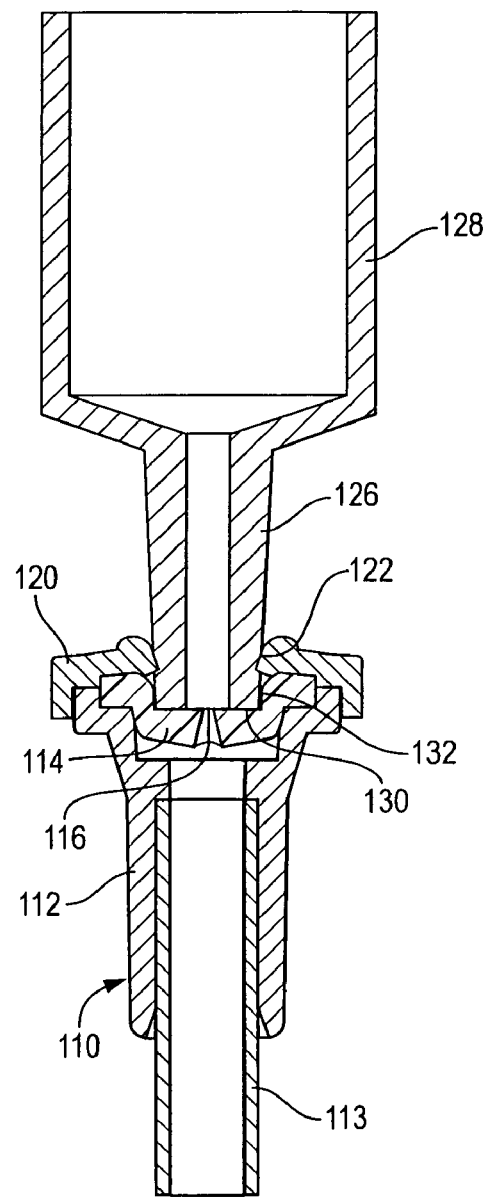

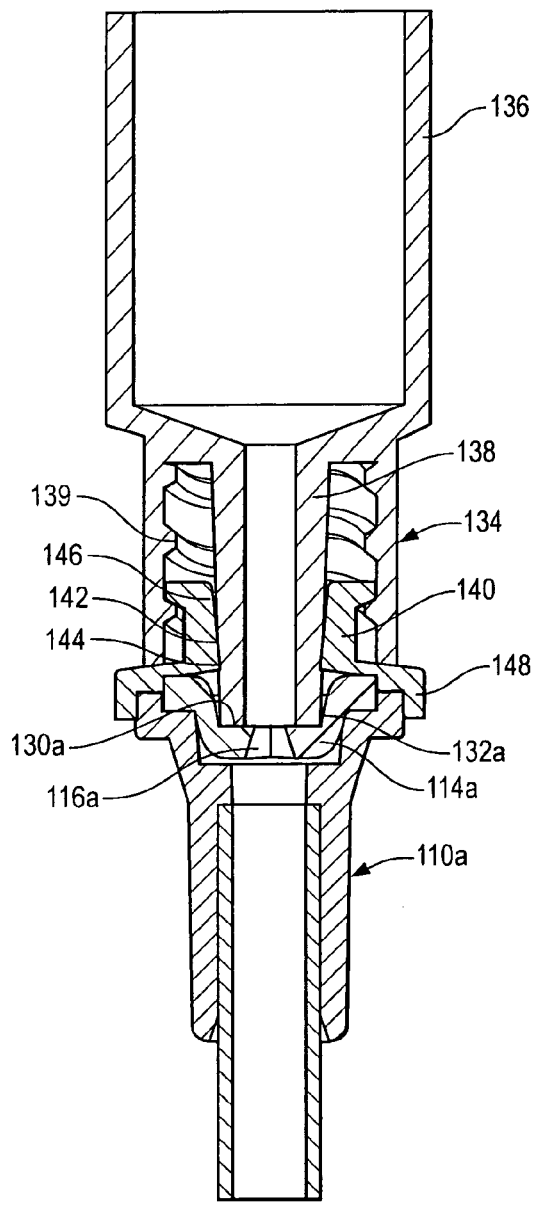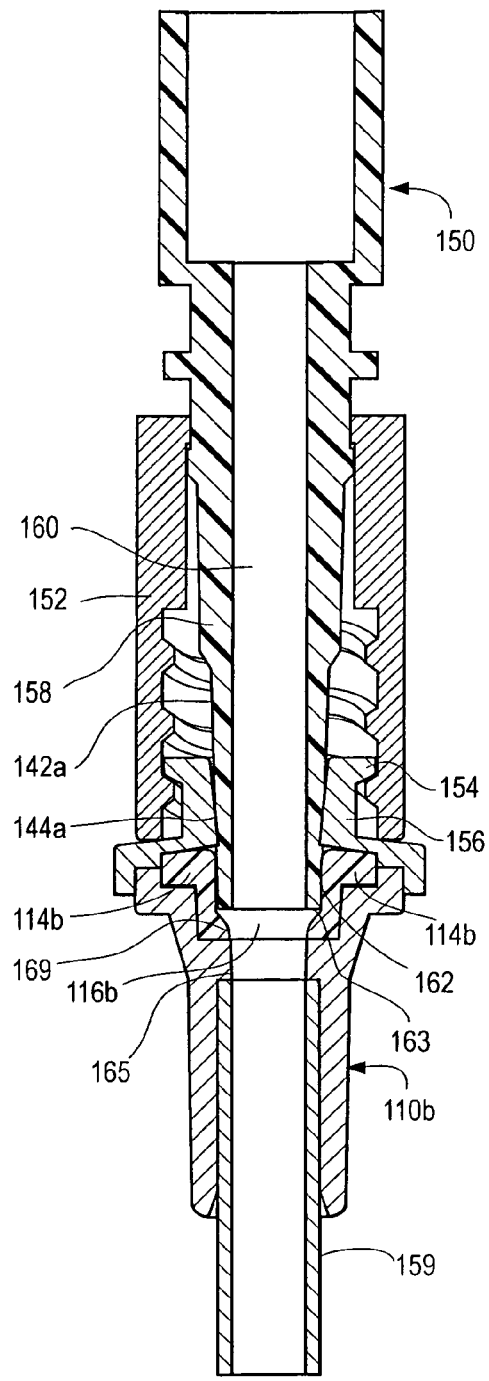

INJECTION SITE FOR MALE LUER OR OTHER TUBULAR CONNECTOR

This is a continuation-in-part of U.S. application Ser. No. 10/264,863, filed Oct. 4, 2002 now U.S. Pat. No. 7,025,744.

BACKGROUND OF THE INVENTION

Tubing sets for the transfer of medical fluids such as blood or parenteral solution generally comprise flexible plastic tubing with end connectors, which are often luer-type connectors. Injection sites are often carried on the tubing at the ends of, or between the ends of, the tubing sets, comprising an elastomeric diaphragm or bung which is carried in a housing in typically compressed or restrained fashion, so that a needle can resealably penetrate the elastomeric bung and communicate with the interior of the tubular set, for administration of medicines and the withdrawal of medical samples such as blood. Also, in the field of extracorporeal blood transport, in which blood is conveyed to and from an extracorporeal blood processing device such as a dialyzer or an aphaeresis apparatus, such an injection site may also be used to add parenteral solution such as normal saline.

As a disadvantage, a needle cannot connect with a luer connection and vice versa. The Medic® Universal Connector of Medisystems Corporation, described by U.S. Pat. No. 5,071,413, is a device which is capable of alternatively penetrating an elastomeric diaphragm and joining with a female luer site in the traditional fashion. However this device is not suitable in all uses. For example, an injection site on a flexible tube set may not fit with the Medic design because the Medic device is too long, and impinges the opposite wall of an injection site carried on tubing, having an entry direction perpendicular to the axis of the tubing.

As a further disadvantage, there may be a need to make a connection through an elastomeric diaphragm injection site using a tube which is terminated in a male luer connector. Present means for doing this are cumbersome. See U.S. Pat. Nos. 5,242,393 and 6,344,033.

By this invention, a connection system is typically provide for medical devices, including vials and containers for medicine, liquid, or gas, and also injection sites mounted on tubing sets. This system is capable of establishing connection with a male luer, including many ISO compatible, commercially available male luer lock connectors, while it is also preferably capable of providing resealable needle connections. Non-luer tapered tubular, tapered or non-tapered probes may also be connected with the system of this invention.

DESCRIPTION OF THE INVENTION

In accordance with this invention, an injection site is provided as part of a medical device which has an interior for containment of a fluid (liquid or gas). For example, the medical device may be a drug vial or container which utilizes the injection site of this invention, or it can be a tubing set having a main flow path for blood, parenteral solution, gases, or the like, to permit access preferably either by a male luer (luer slip or luer lock) connector or other type of tubular probe, without any intermediate device as in the prior art, such access being to the flow path of the tube set or the interior of any other container. Preferably, access through the injection site is also available as well by a needle, sharp or blunt.

An opening is defined into the interior of the medical device, with an elastomeric wall forming a fluid/air tight barrier across said opening, preferably both at positive and negative pressures relative to atmosphere. The elastomeric wall typically defines a compressed, or at least constrained, sealed perforation extending at least nearly therethrough. This perforation may be a closed slit with one or many branches, as in the form of a star (*). It may comprise one or more curved slits, or a simple, straight slit. Optionally, a retaining skin or skins made of another material, or wall material, may prevent complete opening and passage of fluid through the perforation until desired. Also, typically, the elastomeric wall is compressed generally at its periphery, to cause pressurization of the perforation so that there is better sealing through the slit and some resistance to opening, as well as sealing to prevent tears around the elastomeric wall. Alternatively, it is possible to co-mold the elastomeric part and the housing parts in one operation, and in this and other instances the elastomeric wall will not be compressed at its periphery, since it will be held by the molded part in non-compressed but restrained condition. Also wall materials may preferably be used that exhibit cohesion or tackiness between the edges of the slit or perforation to hold it together in releasably closed position.

A retention wall is provided, being generally rigid and nonelastomeric, and located to retain a peripheral portion of the elastomeric wall in its position. The peripheral portion of the elastomeric wall typically comprises an outer ring portion that is secured by the retention wall against an annular seat, with a central portion of the elastomeric wall being exposed to the exterior and said opening. A portion of the retention wall may be spaced from the elastomeric wall. The retention wall has a retention zone surrounding said opening, which zone is that part of the retention wall that engages (i.e. touches) and frictionally retains a connector tube, having a leading end, which is advanced into said opening to partially displace a central portion of the elastomeric wall into said opening and to open a flow aperture (perforation) through the elastomeric wall, for flow through said wall and connector tube. The flow aperture may be provided by a pre-formed perforation, or the connector tube may have a sharp point or edge to open a flow aperture by cutting through a elastomeric wall which does not have a perforation.

The retention zone may be adjacent the elastomeric wall or, alternately, the retention may be placed spaced from the elastomeric wall such that said elastomeric wall is first engaged by the connector tube prior to engaging with the retention zone.

To keep the elastomeric wall in the deformed, open-slit position, at least part of the retained connector tube, or the retention zone, may be made of a material of sufficient hardness that the material of the other of the retained connector tube and the retention zone is deformed, temporarily or permanently, by engagement of the two elements, to increase strength of retention (i.e. resistance to disconnection) between the retention zone wall and the connector tube. Such retention resulting from the deformation may preferably be at least about 100 grams of added force required for such disconnection. The retention zone may deform the connector tube, or vice versa, forming a generally annular indentation and seal therein, to increase the strength of retention between the retention zone and the connector tube.

Also it is preferred for the retention zone to be sized to engage and hold the connector tube before the connector tube's leading end penetrates the elastomeric wall, although the connector tube may have advanced sufficiently to push open the perforation in the elastomeric wall. This can be accomplished in various ways. In one preferred embodiment, the connector tube may be an ISO standard male luer connector tube that tapers outwardly from its outer or leading end to its inner base. Thus, in the embodiments described, the advancing connector tube comes into engagement with the retention zone, where it may be stopped and held, with material deformation to increase the strength of retention, as the connector tube opens the perforation in the elastomeric wall, but before the leading end or outer tip of the connector tube passes beyond (and preferably before passing into) the slit of the elastomeric wall. This preferred condition is shown in all of the specific embodiments of the drawings, including FIG. 13, except for FIG. 19.

Advantages of this include the fact that, with such limited penetration, the connector tube and elastomeric wall will not project far into said opening, which may comprise a blood flow path. Such penetration can cause turbulence, and can reduce the laminar flow of blood through the blood flow path, which is undesirable. Also, such limited penetration, while effective to achieve fluid flow through the elastomeric wall, permits a smaller device to be designed and used, compared with systems where full penetration of the elastomeric wall by the connector tube takes place. Also, as is illustrated in the preferred embodiment of FIG. 13, there are laminar flow advantages available to a connector tube that does not fully penetrate the elastomeric wall, and may be located adjacent a blood flow pathway. The almost-penetrated elastomeric wall serves as a transition and flow guide between the annular end face of the connector tube and the lumen wall of the adjacent connector bore. In typical male/female connector sets, the flow path must exhibit a "step out" from the connector tube to the adjacent bore with significant pressure losses, dependant on the size of the annular face. By this invention, such a step is largely avoided, thus reducing turbulence.

Preferably, the retention zone may be ring-shaped, and may have an axial depth (i.e. its dimension in the generally axial direction of the retained connector tube) of no more than about 3 or 4 mm. In some embodiments, the retention wall may comprise a transverse wall having an aperture that defines the central opening with a thickness of no more than about 1 mm, so that the edge of the wall that defines the central opening can dig into and deform a portion of the retained connector tube, which connector tube may typically be conical in shape. As one advantage of such a configuration, the molding tolerance of the respective parts can be relatively low when compared with a luer connection. For example, it is generally necessary for the retained connector tube to be positioned in its engaged and retained position with its tip extending into engagement with the elastomeric wall to deflect the elastomeric wall, (or optionally to penetrate it) to open the perforation of the elastomeric wall so that flow communication can take place through the elastomeric wall and the retained connector tube. However, the overall dimensions and the longitudinal position of the connector tube may have a certain amount of variability (tolerance) and it still may be advanced into engagement with the elastomeric wall, with material deformation taking place by engagement of the connector tube and the retention zone and the necessary position achieved. Thus, the parts of the device are easier to manufacture. Because material is deformed, in some embodiments the retention tube can advance further relative to the retention zone after an initial contact is made, contrary to a male/female luer connection, for example. Thus part tolerance can be less.

This is particularly important in the case where the retained connector tube is part of an ISO male luer lock connector, where the luer of such connectors only extends a short distance beyond its locking sleeve (such as 2.1 to 3.5 mm), and the advancement into displacement of an elastomeric wall is thus of limited distance. In this embodiment, the male luer does not penetrate through the elastomeric wall, but merely may displace its central portion by a distance sufficient to stretch open the perforation of the elastomeric wall. Upon such advancement, the retention zone surrounding the central opening forcefully engages the male luer of the luer lock connector, with deformation of material resulting through such engagement in one, or the other, or both parts, to increase friction strength of retention between the retention wall and the male luer connector tube, so that the natural resilience of the displaced elastomeric wall does not force expulsion of the connector tube from the retention zone, and a stable, open flow path is created. This arrangement is especially good for connectors used in blood flow tubing, since a turbulence and clot promoting male luer tip in the blood flow path is avoided.

Preferably, the material of one of the retention zone and the connector tube is harder than the material of the other part, to facilitate deformation of material as engagement between the connector tube and the retention zone takes place, resulting in increased strength of retention between the retention wall and the connector tube. Depending on the design and nature of the materials, this engaged and retained relationship between the connector tube and the retention zone may be permanent or temporary, but preferably is of sufficient strength that accidental separation does not take place. Typically, the retention zone is harder than the connector tube, having a Shore A durometer of at least about A80.

Preferably, the elastomeric wall comprises a flexible barrier having a width at least as great as its depth positioned across the opening. Typically, the elastomeric wall is substantially greater in its width than its depth. A retention wall may be positioned to retain the elastomeric wall in sealing relation to said opening. The retention wall defines a central opening. The elastomeric wall has a periphery which is retained in fixed position relative to the retention wall, with the retention wall having a retention zone surrounding the central opening to engage and retain the connector tube, which connector tube has a leading end which is advanced into the central opening to press against and, in some embodiments, to displace a central portion of the elastomeric wall. This displacement of the elastomeric wall can open a perforation defined through the elastomeric wall for flow through the wall and connector tube. Alternatively, if desired, the displacement of the elastomeric wall may not necessarily open the perforation, but said displacement reduces the pressure resistance to flow at least in the displaced direction of such perforation, while not in the other direction so that pressurized fluid flow can then open the perforation, while normally pressurized fluids cannot open the perforation in the displaced direction.

As described above, the retention zone may be made of a material of greater hardness than the material of the engaged and retained connector tube so that the retained connector tube is deformed at the retention zone with the generally annular indentation described above by engagement with the retention zone, to increase the strength of retention between the retention wall and the connector tube. As stated before, the retention zone may be sized to engage and retain the connector tube before the leading end actually enters the perforation.

Preferably, the elastomeric wall comprises a generally flat partition, rather than a partition which is of increased depth by having axially extending members, for example, as in Frank, et al., reissue U.S. Pat. No. 35,841. Such a generally flat partition may define a central dome portion if desired, particularly a dome that extends away from the advancing connector tube, which tends to increase the resistance of the perforated elastomeric wall to outward flowing of pressurized fluid. Also, the elastomeric wall may be truly flat, without a dome, if desired. Both of these structures distinguish from flexible barriers that have significant axially extending portions, particularly when such portions extend axially farther than the width of the elastomeric wall.

In some embodiments, the retention zone may have an axial depth of no more than about 3 or 4 mm, and preferably no more than about 0.6 mm, being sized to engage and hold the connector tube to prevent the leading end thereof from penetrating the perforation, while allowing it to displace a central portion of the elastomeric wall to open the perforation for fluid flow.

Preferably, the connector tube is part of a conventional male luer lock connector which comprises a male luer and a locking ring, the male luer having a tip projecting forwardly beyond the locking ring by no more than about 3.5 mm, preferably complying with ISO specifications. The male luer extends through the retention wall central opening sealingly and engages the retention zone carried by the retention wall, when in connection with the device of this invention described above. In some embodiments, the male luer has a tip engaging the outer surface of the elastomeric wall, and typically surrounding but not penetrating the perforation defined in the elastomeric wall, while pressing against the elastomeric wall to deflect it inwardly, stretching the perforation toward an open, fluid flow permitting position. Thus an additional fluid-tight, annular seal may be formed between the luer tip and the elastomeric wall. The locking ring has an outer end that abuts the retention wall, to prevent further advancement of the male luer at its position of engagement. The retention wall may be of a thickness that positions the male luer beyond its locking ring to deflect the elastomeric wall, to cause stretching of the perforation without allowing the male luer to enter the perforation.

In some embodiments, the retention zone may be defined by a ring which projects inwardly from a tubular wall that comprises at least part of the retention wall extending perpendicularly, outwardly from the elastomeric wall. Typically, this tubular wall surrounds said opening, and extends from an annular cap structure that is also part of the retention wall, and which engages the elastomeric wall at its periphery for retention thereof by pressing the periphery against an annular seat.

The above described ring may be of a harder material than the material of the male luer, so that the annular indentation described above is formed in the male luer, increasing strength of retention between the retention wall and the male luer connector tube.

In some embodiments, a plurality of typically radial spaces may divide the retention zone into separate sections, to provide for greater flexibility of the material of the retention zone, for example, as when the retention wall and its retention zone are made of a metal, such as stainless steel. In such a situation, separate tab edges of the retention zone can engage the connector tube and dig into the material of the connector tube, for firm retention as the tip of the connector tube displaces a central portion of the elastomeric wall and opens a perforation defined therein, for fluid communication through the wall and connector tube.

Typically, the axial distance by which the connector tube of the ISO type displaces the elastomeric wall at its center is on the order of 1 to 4 mm or sometimes up to 6 mm, in those circumstances where the connector tube does not penetrate through the elastomeric wall perforation, but its front end presses axially against the surface of the elastomeric wall, generally with a closed loop sealing line of pressure positioned on the elastomeric wall, typically radially beyond any portion of the perforation, to provide a closed, preferably fluid tight sealing area between the end of the connector tube and the elastomeric wall.

If the connector tube does displace the elastomeric wall further, but without the front end actually penetrating into or beyond the perforation slit, an added seal may be provided between the connector tube side wall and the surface of the elastomeric wall. The connector tube may further displace the elastomeric wall where the front end of the connector tube does penetrate through the perforation of the elastomeric wall, in which case the only seal remaining may be provided between the connector tube and the material defining the perforation. The perforation may be proportioned in some embodiments to provide a 360 degree seal about the connector tube side wall, to provide a seal in a different way from abutment of the tip of the connector tube against the elastomeric wall around the area of the perforation, as discussed in the last paragraph.

Also, as illustrated in the drawings, a combination of the above two seals may be obtained, where the front end of the connector tube presses against the elastomeric wall, and deflects the elastomeric wall to a degree that the wall provides a second 360° seal about the connector tube sidewall. See particularly, FIGS. 11-13 for this feature.

Typically, the injection site does not require lubrication of the elastomeric wall with silicone or the like, avoiding the problem of silicone build up in the body.

In some embodiments, the perforation may comprise a line having a length of about the outer diameter of a male ISO luer at a point adjacent to its minimum diameter end, which line can stretch to provide the desired 360 degree seal as the luer penetrates into the perforation. Such a system may be used with a luer slip or a luer lock system.

In some embodiments, upper and lower retention wall portions for retaining the periphery of the elastomeric wall may respectively define upper and lower central apertures which are positioned generally coaxially with each other. The lower central aperture of said opening may be of greater diameter than the upper central aperture of said retention wall, which facilitates inward displacement of the elastomeric wall by the connector tube, to cause opening of the perforation. The retention zone may then be defined around the central upper aperture. Typically, the lower central aperture is rarely smaller than a 4 mm inner diameter, and may need to be larger, so as to allow enough "doming downward" of the elastomeric wall to allow sufficient stretching by an ISO male luer which has a leading outer diameter of 3.925 to 4.027 mm. Alternatively, the lower retention member may exist on its own, without an upper retention member, and may be dimensioned to grip the side wall of the connector tube with or without a stretched, displaced elastomeric wall intervening between the connector tube and said lower retention member.

In some embodiments, there may extend outwardly from the elastomeric wall and the retention wall a tapered-bore tube having opposed, longitudinal slots, to permit easier antiseptic swabbing of the interior and the outer face of the elastomeric wall, at the same time providing locking connection to a connector tube. Alternatively, such a tube may have a cylindrical bore or a counterbore with or without such slots or it may comprise a female luer or luer lock device.

It can also be seen that it is generally possible to make connection through the injection site of this invention by conventionally using a hypodermic needle, where the sharp needle passes through the body of the elastomeric wall in normal piercing fashion, or through the at least partially preformed slit. When such a slit is used, it may be possible for a dull point needle to be used for connection.

As stated above, locking systems may be utilized as additional structure for connection so that accidental connector separation can be further eliminated as a risk.

Alternatively, the retention wall and retention zone described above may also be made of a fairly resilient material, so that it does some or all of the deformation, when engaging with the retained connector tube, to have the effect of increasing strength of retention between the retention wall and the connector tube.

Certain IV and hemodialysis sets which are sold by Japan Medical Supply (JMS) and Kawasumi Laboratories disclose transversely-mounted injection sites which comprise slit elastomeric walls, compressed to reseal. The elastomeric wall is partially covered by a top wall in one case, having a central aperture large enough to receive a conventional male luer without a locking ring, which non-locking luer can penetrate completely through the elastomeric wall because of the presence of the slit, and the retention wall provides no restriction against said penetration. Neither of these designs can be opened for two way flow by known ISO standard male luer lock connector designs, even with prior penetration of the slit by another object including an ISO standard male luer lock connector. Nor can male luer locks be retained by the aperture in the top wall of the housing, nor are male luer slips retained by the aperture in the top wall of the housing while avoiding complete elastomeric wall penetration.

The JMS injection site requires the use of a non-ISO intermediate connector, called a Planecta, that fits to a male luer lock at one end and locks to the external housing of the injection site in a bayonet-type fitting.

By this invention, a direct connection can be made with an injection site of this invention and a male luer connector, or a male luer lock connector, particularly those of ISO standard, without any need for an intermediate connecting component. Connection can also be made with a sharp or dull needle, not necessarily in any locking or retained relationship. The inventive injection site, contrary to those of the prior art, is thus capable of providing a direct connection at any time with any of the components listed below and the like, so that the injection site can be connected with a wide variety of conventional medical sets and other items, providing a wide compatibility of use of a medical device which carries the injection site of this invention. The injection site of this invention may be used with an essentially unlimited variety of medical devices, whenever aseptic access is desired. For example, as shown, the injection site may be carried on any of a variety of tube sets in the manner of a T connector as shown in FIGS. 1 and 2, or at a tube end. The injection site may be used on an adaptor of various kinds, a stopcock, or as the stopper in any kind of container or vial for typically medical materials. Thus, the injection site of this invention may be carried by any kind of medical device such as syringes, needles, hubs, fluid transport sets, including IV sets, blood tubing sets, blood bag sets, transfer sets, and winged needle sets. Also, the injection site of this invention may be carried on other medical devices such as medical fluid containers, body access devices, and VACUTAINER™ blood drawing units.

The injection site of this invention, as part of such medical devices, may connect with a great number of different devices which carry a connector tube for connection with the injection site of this invention. For example, the connector tube may be carried by a syringe barrel, a tube set, an adapter, a stopcock, a medical fluid container, a vial or the like.

A preferred injection site of this invention comprises a housing having an interior, an opening to the interior, and an elastomeric wall which comprises a barrier across the opening. The elastomeric wall has a central area which defines a sealed perforation extending at least nearly therethrough. In other words, if the perforation does not extend all the way therethrough, a thin skin layer remains to provide sealing until it is opened by the connector tube as described above, which typically may be a male luer, either a luer slip or part of a luer lock connector, passing therethrough or sufficiently stretching the thin skin until it tears open. This skin layer does not need to be an elastomer, and may fracture when the wall is stretched by the pressing connector tube. For example, the skin layer may be a plastic coating such as a lacquer paint layer.

As another possibility, the sealed perforation of the elastomeric wall may not open at all when connection is made with a connector tube. However, the original seal of the perforation, which is strong enough to seal against substantial positive or negative pressure, is weakened by the deflection of the elastomeric wall by the connector tube so that, while still closed, its pressure resistance may be lowered in the deflected direction (or both directions). Then, flow takes place typically at relatively low trans-wall fluid pressures normally encountered in medical fluid handling, so that fluids can be passed through the elastomeric wall between the connector tube and the injection site of this invention, but resealing takes place when the pressure on both sides of the elastomeric wall are equalized. Such resealing takes place until the pressure differential is created again for added flow. Also, in some embodiments, the shape of the elastomeric wall may comprise a one-way valve, so that pressurized flow at relatively low pressures normally takes place in only one direction and not in the other direction.

In another embodiment, the connector tube may be retained by the retention zone in sealing relationship, without the connector tube being in displacing contact with the elastomeric wall. Thus, a syringe, for example, may be left attached to the inventive device without opening the slit or breaking sterility of the connection.

In another embodiment of the above type, a connected medical device of this invention, connected with a male luer lock connector, carries an elastomeric wall covering the first opening and a retention wall as previously described, where the retention wall defines a central opening aligned with the central portion of the elastomeric wall. The male luer lock connector, which may be an ISO standard connector, has a male luer and a locking ring, with the male luer extending through the retention wall central opening and engaging a retention zone carried by the retention wall to form an annular seal. The male luer has a tip positioned adjacent to an outer surface of the elastomeric wall, but it does not press the elastomeric wall to deflect it inwardly. It may even be spaced from the elastomeric wall, which defines at least one perforation so that pressurized fluid passing through the male luer can deflect the elastomeric wall inwardly (or outwardly, depending on flow direction) and open the perforation, to permit fluid flow through the perforation and the male luer. Typically, the elastomeric wall is in contact with portions of the medical device of this invention only at peripheral portions of the wall, contrary to various prior art structures.

Such a system, when connected with a catheter and subjected to lumen pressure, allows opening of the perforation with a minimum of deflection of the elastomeric wall. Thus, when the pressure is released, the suction which is generated in the catheter as the elastomeric wall retracts is minimal, since the retraction is minimal. Thus, where blood is involved as in dialysis catheters, less blood is sucked into an implanted catheter at the end of a dialysis procedure.

The structure of this invention may be similar to previous structures, where the elastomeric wall has a width that is at least as great or preferably greater than its depth, and in which the elastomeric wall consists essentially of a generally flat partition, and where the retention zone may be made of a material harder than the male luer to form a desired, generally annular indentation in the male luer at the retention zone to increase engagement and strength of retention.

In one aspect of the invention, a connected medical device and a male luer lock connector is provided where the structure is similar to that previously described, with the medical device having an interior for containment of fluids, a first opening into the interior and an elastomeric wall comprising a fixedly placed, flexible barrier across the opening, plus a retention wall positioned adjacent to a peripheral portion of the elastomeric wall and defining a central opening aligned with a central portion of the elastomeric wall, to retain the elastomeric wall in position on the medical device.

In some embodiments, the male luer lock connector may be of a shape conforming to ISO standards, comprising the usual male luer and locking ring in which the tip projects forwardly beyond the locking ring by at least 2.1 mm. The male luer extends through the retention wall central opening, and engages a retention zone carried by the retention wall. The male luer has a tip engaging an outer surface of the elastomeric wall, surrounding but not penetrating at least one perforation defined in the elastomeric wall, while pressing against the elastomeric wall to deflect it inwardly, to stretch the perforation toward an open, fluid flow permitting position. As before, the locking ring has an outer end that engages the retention wall to prevent further advancement of the male luer in its locking position, with the retention wall being of a thickness that positions the male luer to deflect the elastomeric wall inwardly to cause the stretching of the perforation without allowing the male luer to enter the perforation. Preferably, the elastomeric wall is in contact with portions of the medical device only at peripheral portions of the wall.

In some embodiments, a retainer cap comprising upper and lower retaining member portions retains the elastomeric wall fixedly in its barrier position across the opening. The cap defines an area which is typically annular, and which surrounds the central area of the retainer cap. The annular area may have an inner diameter of about 4 to 8 mm and a first upper, peripheral surface. The central area of the elastomeric wall may have a second, upper surface, with a relative level of the second upper surface being no lower than the level of the first upper surface. Because of this, when particularly an ISO standard male luer connector is advanced to open the injection site, the outer, annular end of the male connector skirt can rest against and form the closed loop seal that surrounds the central area, and the central male luer, which projects beyond the connector skirt by a predetermined amount, distorts the elastomeric wall sufficiently to open the sealed perforation for fluid communication through the barrier and to form another annular seal around the perforation.

Furthermore, the central area of the elastomeric wall may typically have a thickness of no more than 3 mm. Also, it is generally preferred for the second upper surface (of the central portion of the elastomeric wall) to have a level that is above the level of the first, upper surface of the closed loop area against which the male luer lock connector may abut. This provides more distance of displacement of the elastomeric wall when it is opened, when compared with prior art injection sites.

In some embodiments, a medical valve connector is provided having an interior for containment of fluids; an opening into the interior; an elastomeric wall having at least one closed perforation and comprising a fixedly placed, flexible barrier across said opening, and a retention wall positioned adjacent to a peripheral portion of said elastomeric wall. The retention wall also defines an outwardly extending socket tube portion, having a bore that communicates with a central portion of the elastomeric wall. The socket tube portion defines an annular retention zone along part of the length of the bore of the tube portion.

The socket tube portion further defines an outer, frusto-conical bore portion having a first wall angle, and an inner bore portion having a second wall angle that is less than the first wall angle (or it may be parallel to the bore axis-an angle of zero or even counter-board). The socket tube portion is proportioned to receive a connector tube and deform at the retention zone by physical contact and physical deformation between the connector tube and at least part of the inner bore portion, to provide good retention between the connector tube, having increased retention strength because of the physical distortion, and also for the purpose of forming an annular seal, which may be fluid tight.

The connector tube may be so positioned in the socket tube bore, defining the physical contact, the physical deformation, and the annular seal of the retention zone, while the tip of the connector tube remains spaced from the elastomeric wall. Alternatively, the connector tube may be further manually advanced, with physical deformation in the retention zone, while retaining the annular seal intact as the connector tube advances, to permit the connector tube tip to press against and to deflect the elastomeric wall to open the perforation in a manner similar to previous embodiments. Thus, this connector and an attached connector tube can have a plurality of positions, in which the connector tube tip is either spaced from the elastomeric wall, or it deflects the elastomeric wall in a manner similar to the previously described embodiments.

Each of these positions has an advantage, so it is advantageous to provide a valved connector system in which both positions can be utilized, and in which the annular seal does not need to be broken as one moves between the two positions.

It should be noted that this ability to move between two sealing positions is not found, for example, in the simple luer connector. It that system, when connection is made, sealing is achieved, and no further advancement of the male luer is possible. To the contrary, many of the embodiments in accordance with this invention have contact between the valved connector and the connector tube only at a retention zone which is of a length significantly less than the entire length of the valved connector and connector tube, which is generally contrary to the situation as found in luer connectors. Because the retention zone, which is defined by the area of physical contact between the two parts, is shallow, typically having a depth of no more than about 4 mm, it becomes possible to achieve the physical deformation of material of the connector tube and/or the socket, which is typically part of the retention wall, so that manual deformation between the parts may take place, resulting in both retention and creation of a liquid tight, annular seal. However, because of the small area of the retention zone, the connector tube may be further manually advanced after such a seal is formed, to go from a position that is spaced from the elastomeric wall to a position that deflects the elastomeric wall to open the perforation, in a manner similar to the previous embodiments.

An advantage of the advanced position, where the connector tube deflects the elastomeric wall and stretches open one or more perforations, is that there is little resistance to flow passing through the slit when it is open. Thus, it may be desired to use this position when a relatively large amount of fluid is being administered to a patient through a syringe, or in the situation where parenteral solution or blood is being administered to a patient by the use of a gravity head, involving low pressures. However, as a disadvantage, particularly relating to catheters which connect long term with a blood vessel of the patient, clotting is generally suppressed by administering a bolus of heparin with a syringe to fill the catheter for a storage period between uses. As the syringe is then withdrawn, the deflected elastomeric wall retracts to its original position, exerting a suction in the catheter, which causes some blood to be drawn into the distal tip of the catheter in the blood vessel. That blood becomes stagnant and tends to clot, which of course is known to be highly undesirable.

Accordingly, after use of the catheter, when it is desired to fill its interior with heparin solution, for example, to preserve an indwelling catheter with access to a blood vessel, the first administration position may be provided, in which the connector tube is spaced from the elastomeric wall while it still participates in an annular seal at the retention zone. A small bolus of heparin may be administered through the catheter to fill it with less deflection of the elastomeric wall, since the fluid passes through the perforation with the minimal deflection. Then, when that process is finished and the fluid is no longer pressurized, the retraction of the elastomeric wall to its original position is much less, resulting in much less suck back of blood, or preferably none at all, at the distal tip of the catheter. Accordingly, this two-positioned valve connector system can provide significant advantages of use, especially when working with medical devices connected to conduits that carry blood and are connected to a blood vessel.

DESCRIPTION OF THE DRAWINGS

In the drawings.

FIG. 3 is a longitudinal sectional view of an embodiment of an injection site and connector of this invention, carried on one end of a housing which, in turn, connects with an end of flexible tubing of a medical tube set.

FIG. 4 is a plan view of the retention wall used in FIG. 3.

FIG. 5 is a longitudinal sectional view of the injection site and connector of FIG. 3, shown to be in connected relation with an ISO male luer connector which is part of a syringe.

FIG. 10 is a longitudinal sectional view of another embodiment of an injection site and connector of this invention, shown in separated relation with a conventional luer slip (i.e. non-luer look) connector.

FIG. 11 is a longitudinal sectional view showing the components of FIG. 10 connected together to provide a flow connection between them.

FIG. 12 is a longitudinal sectional view of another embodiment of the injection site and connector of this invention, with modification, and connected to a conventional luer lock connector.

FIG. 13 is a longitudinal sectional view of another embodiment of the injection site of this invention shown to be connected to a luer lock connector having a rotatable, threaded luer lock sleeve.

DESCRIPTION OF SPECIFIC EMBODIMENTS

Figure 1:
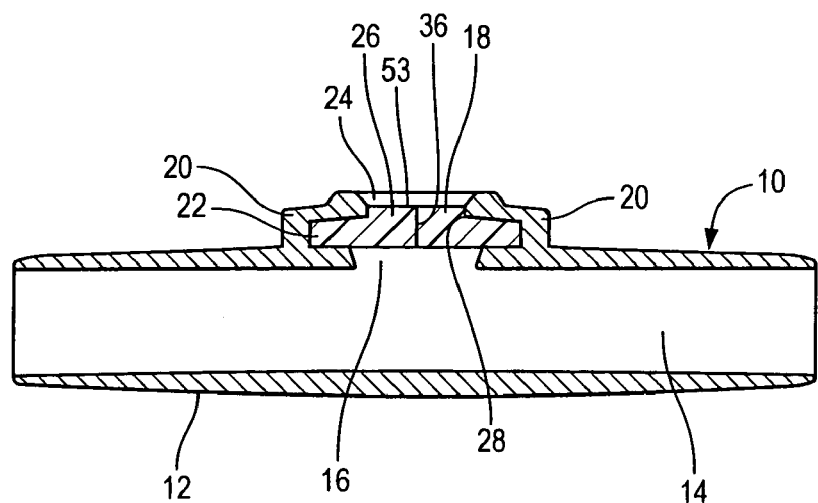
FIG. 1 is a longitudinal sectional view of an embodiment of an injection site of this invention mounted on a tubular section, for connection with other tubular sections to form a tubular set for medical fluids.

Referring to the drawings, FIG. 1 shows a medical device 10 which comprises both a connector for a male luer or other tube, and an injection site. Device 10 shows a length of typically rigid tubing 12 which has an interior 14 for containment of fluid. Tubing 12 may connect at both ends with lengths of flexible set tubing for blood or parenteral solution. For example, the sets which carry generally rigid tube 12 may be arterial or venous sets for hemodialysis, pheresis, or the like.

Tube 12 defines a lateral opening 16 to the interior and a fixedly placed, flexible barrier 18, which may be an elastomeric wall extending across the opening.

A retention wall 20 is positioned adjacent to a peripheral portion of elastomeric wall 18, comprising an outer housing portion which may be a glued, heat welded, or ultrasonic welded to an annular rib 22 of tubular housing 12. Retention wall 20 defines a central opening 24, which exposes a central portion 26 of elastomeric wall 18.

Figure 2:
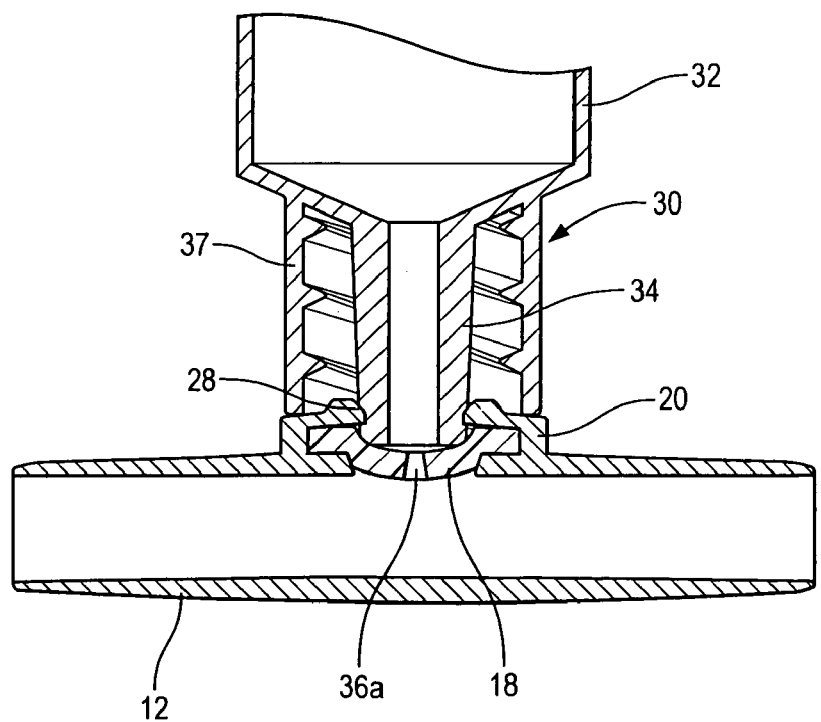
FIG. 2 is a longitudinal sectional view of the injection site of FIG. 1, shown to be in connection with an ISO male luer lock connector carried on a syringe.

Retention wall 20 defines an annular retention zone 28 surrounding central opening 24, to engage and retain a connector tube 34 which is advanced into the central opening, and to form an annular seal, as shown in FIG. 2.

Specifically, FIG. 2 shows a male luer lock connector 30 carried on the end of syringe 32, and defining male luer (connector tube) 34 and threaded locking sleeve 37. Specifically, luer lock connector 30 is of dimensions and other characteristics which are compatible with the standards of the ISO (International Standards Organization) Standards 594-1 and 594-2, as are most luer connectors available for clinical use.

As seen in FIG. 2, connector tube 34, which is the male luer, advances through central opening 24. As connector tube 34 advances, it displaces elastomeric wall 18 and opens a flow aperture 36a by expanding preformed slit or perforation 36, which is previously formed in elastomeric wall 18. However, in this embodiment tube 34 does not enter slit 36. At the same time, annular retention zone 28 of retention wall 20 is made of a plastic or metal which is hard enough to cause deformation of the plastic of male luer connector tube 34. Because of such deformation, there is an increase in the strength of retention at the junction between retention zone 28 and male luer 34, so that luer connector 30 is not readily withdrawn from its position shown in FIG. 2, without the intentional use of substantial withdrawing force, this being despite the fact that elastomeric wall 18 has a natural elastic resistance to its position shown in FIG. 2, and thus urges male luer connector outwardly. Thus, retention is provided at the junction between retention zone 28 and connector tube 34. Accordingly, syringe 32 may be held in flow connection with tube 12, which is typically part of a medical fluid flow set, so that desired materials may be passed into the flow set which carries tube 12 from syringe 32.

Retention wall 20 and annular retention zone 28 may be molded of an acrylic material, particularly, Cryolite Med 2 modified acrylic plastic, manufactured by Cryo Industries of Rockaway, N.J., having a Rockwell M hardness of 33. This is harder than the typical polypropylene of which a typical male luer connector may be manufactured, so that deformation of male luer 34 can take place, to strengthen the retention between retention wall 20 and male luer 34 when they are joined together as in FIG. 2. Tubular housing 12 may also be made of an acrylic material.

As a further advantage, if the flowing fluid in the set which comprises tube 12 is blood, little turbulence and flow blockage is created by the connector of this invention, less than an inwardly projecting spike, for example. Hence, fluids may be added to the set without disrupting a laminar flow path through the set, which facilitates the reduction of blood clotting.

Syringe 32 may then be separated by a positive twist and pull from the injection site comprising retention wall 20, and elastomeric wall 18 closes slit 36 again for sealing of the system.

Alternatively, the injection site comprising retention wall 20 also permits needle access, both by a sharp needle penetrating through the elastomeric wall 18, or a dull needle, which can pass through slit 36.

The vertical thickness of the annular retention zone 28 which extends around connector tube 34 can be about one millimeter or less. Also, an internal, annular thinner edge may be defined at the retention zone 28 to facilitate the deformation of material. That strengthens the retention between retention wall 20 and connector tube 34, with the annular edge digging into the outer surface of connector tube 34.

Referring to FIGS. 3-5, another embodiment 40 of the medical device of this invention is carried on the end of tube 42, which may be a molded structure capable of receiving a flexible tube of a medical tube set for blood or parenteral solution, and serving as an injection site. Tube 42 may also comprise part of a Y site, a T site, or the like.

Tube 42 terminates in a generally rigid head portion 44, which comprises an annular support surface 46 for carrying the peripheral portion 48 of elastomeric wall 50. Elastomeric wall 50 may have an optional perforation 52, or it may comprise an intact wall, which is perforated immediately prior to use, for example, either by a separate, pointed instrument or by a tube generally of the shape of a male luer, but with a spike carried on the front end. Elastomeric wall 50 comprises the fixedly placed flexible barrier, being retained in position by retention wall 54, which may comprise a metal or plastic cap having a central aperture defined by closed loop retention zone 56 of retention wall 54. It can be seen that retention zone 56 comprises a small inner, bent, annular portion so that inwardly facing, sharp, annular edges may be defined.

FIG. 4 comprises a plan view of retention wall 54, showing central opening 58 and the inwardly facing, annular retention zone 56. In this embodiment, retention zone 56 comprises a material having a hardness of at least about Shore A 90, and divided into separate sections by radial slots or spaces 60, so that the individual separate retention zone sections 59 exhibit a measure of flexibility, but are still rigid enough to exhibit strong retentive characteristics against a connector tube 34*a* with which they engage as the tube enters into central opening 58, deforming material of connector tube 34*a* for strengthened retention.

Such an entrance by connector tube 34*a* is shown in FIG. 5. As in the previous embodiment with respect to luer lock connector 30, this luer lock connector 30*a* is connected to a syringe 32*a*, and comprises the male luer 34*a* and a threaded locking sleeve 37*a* in conventional manner.

As shown in FIG. 5, the connection is made by forcing male luer 34*a* inwardly within annular retention zone 56, until outer, annular end 62 of locking sleeve 37*a* abuts retention wall 54. The advancing male luer 34*a*, being of frustoconical shape, tightly engages retention zone 56 on such advancement, with deformation of plastic material at the junction area 56, to increase strength of retention between retention wall 54 and male luer or connector tube 34*a*, to provide a locked connection, which may be a releasable lock if desired. This also causes the displacement of the central portion of elastomeric wall 50 by male luer 34*a*, in a manner similar to the previous embodiment, resulting in the opening of perforation 52, which opens a fluid flow path between tube 42 and syringe 32*a*.

When it is desired to withdraw syringe 32*a*, it can typically be simply pulled or twisted and removed, and elastomeric wall 50 springs back into its normal position of FIG. 3, closing perforation 52.

It should be noted that in its natural configuration as shown in FIG. 3, the upper, central surface 53 of elastomeric wall 50 is elevated relative to the corresponding upper surface of the peripheral portions of the elastomeric wall, and it even may project above retention wall or retainer cap 54. As previously stated, this permits greater deformation of elastomeric wall 50 when a luer lock connector 30*a* is brought into engagement as in FIG. 5 which, in turn, can provide better opening of perforation 52.

As can be seen in both embodiments of FIGS. 1-5, the male luer 34, 34*a* has a tip projecting forwardly beyond the locking sleeve or ring 37, 37*a*, and is shown to abut against retention wall 20, 54 in the respective embodiments. This of course limits the forward advancement of male luer 34, 34*a* so that elastomeric wall 18, 50 is displaced by an amount which is enough to open perforation 36*a*, 52, without providing so much advance of the male luer 34, 34*a* that it penetrates into the respective perforation 36*a*, 52, but instead forms a fluid tight, annular end seal between the distal end of male luer 34, 34*a* and the upper surface 53 of elastomeric wall 18, 50. In each case, the tip of the male luer engages the outer surface of the elastomeric wall to surround but not penetrate the perforation defined in the elastomeric wall, while pressing against the elastomeric wall to deflect it inwardly, stretching the perforation toward an open, fluid flow-permitting position. This particular positioning of maximum, advancement of the male luer can be controlled by controlling the thickness of retention wall 20, 54, particularly at position 62, where the outer end of locking sleeve 30, 30*a* engages the retention wall, so that the maximum advanced position of male luer 34, 34*a* can be controlled to achieve the desired results.

Figure 6:
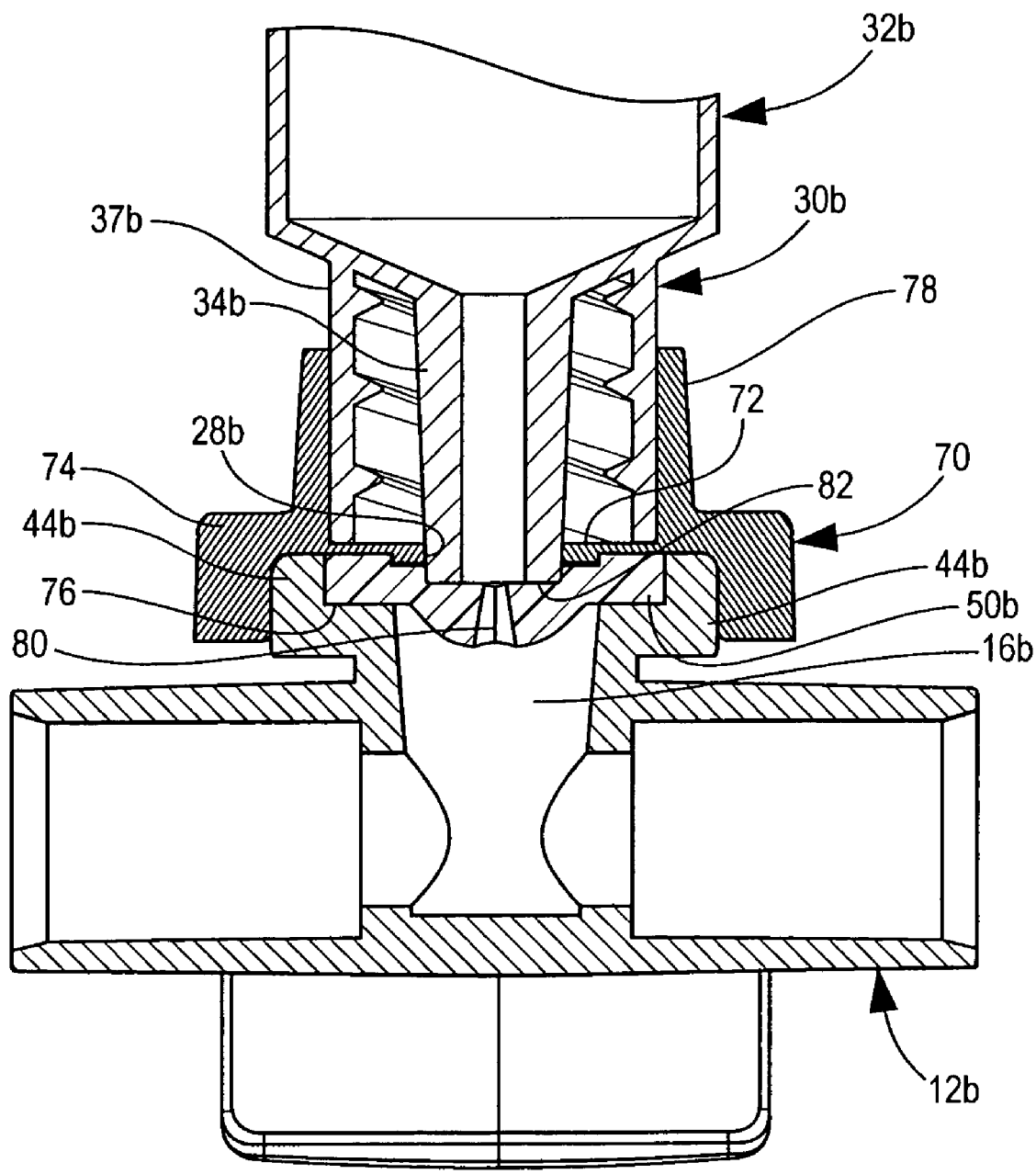
FIG. 6 is a vertical sectional view of another embodiment of this invention in connected relation with an ISO male luer connector which is part of a syringe.

Referring to FIG. 6, injection site 70 is shown, being generally similar in structure and function to the previous injection sites disclosed, except as otherwise specifically described herein. Container or syringe 32*b*, having a male luer lock connector 30*b* comprising locking sleeve 37*b* and male luer 34*b*, is shown to be in connection with injection site 70. Container or syringe 32*b* may be identical to the previous containers or syringes 32 and 32*a* as shown in previous drawings.

In this particular embodiment, retention wall 72 comprises a plastic plate, carried integrally with a molded cap member 74, which serves to hold elastomeric wall 50*b* in the desired position on annular seat 76, so that the periphery of elastomeric wall 50*b* may be compressed and retained in desired position. Wall 50*b* is carried on head portion 44*b*, which defines a lateral opening 16*b* in molded tubular component 12*b* which is a tubular structure which may be connected at both ends with lengths of flexible tubing of a flow set for blood or parenteral solutions. Cap member 74 may be solvent sealed, snapped over, or otherwise bonded to head portion 44b for nonremovability during normal use.

In this embodiment, cap portion or cover 74 has an upstanding sleeve 78, which is without threads or other structure, for retention of male luer lock member sleeve 37b. It can be seen that male luer 34b extends through an aperture in retention wall 72, with retention wall 72 being made of plastic, metal, or the like. As ISO standard male luer connector 34b passes through the aperture defined by retention wall 72, its outer wall attains greater dimension by its conical nature, until locking sleeve 37b enters into engagement with retention wall 72. At the same time, male luer 34b, typically projecting outwardly beyond locking sleeve 37b by approximately 2.1-3.5 mm., deflects the central portion of elastomeric wall 50b to open perforation 80 in a manner similar to the previous embodiments. The outer wall of male luer member 34b forcibly engages retention zone 28b, to cause the deflection of material at the annular junction site (28b) to cause deformation of material of one or the other components at the annular junction site 28b, to increase the strength of the bond between syringe 32b and connector device 12b. In the connected configuration, slit 80 opens, for flow communication through slit 80 and male luer 34b to and from the interior of tube 12b.

The forward advancement of luer 34b is governed by the diameter of the aperture defined by retention zone 28b. Thus, the degree of distention of elastomeric wall 50b can be controlled so that luer 34b does not overstretch slit 80 and enter into it, when that is desired. Also, the formation of an annular seal line 82 between the distal end of male luer 34b and the upper surface of elastomeric wall 50b provides a further, desirable sealing of the flow path through perforation 80 and male luer 34b.

The impinging relation between retention zone 28b and male luer 34b can cause material deformation, typically in male luer 34b when annular retention zone 28b is made of harder material, to provide frictional and mechanical retention between the two pieces, so that they are not easily separated by accident. Retention wall 72 may be made of a plastic that is harder than the plastic of male luer 34b, although the opposite may be utilized when desired, to obtain similar results.

Also, as luer lock connector 30b is advanced to the position shown in FIG. 6, the outer wall of luer lock connector sleeve 37b can make contact with the inner wall of upstanding sleeve 78, to provide frictional securance, and further assurance of retention of the two components together in a locked, flow permitting relationship, so that the contents of syringe 32b can flow into tubular member 12b, which may comprise part of a set for the transport of blood or parenteral solutions. If desired, the circular aperture-defining retention zone 28b of retention wall 72 may be serrated to facilitate a digging-in action for retention of male luer 34b.

Figure 7:
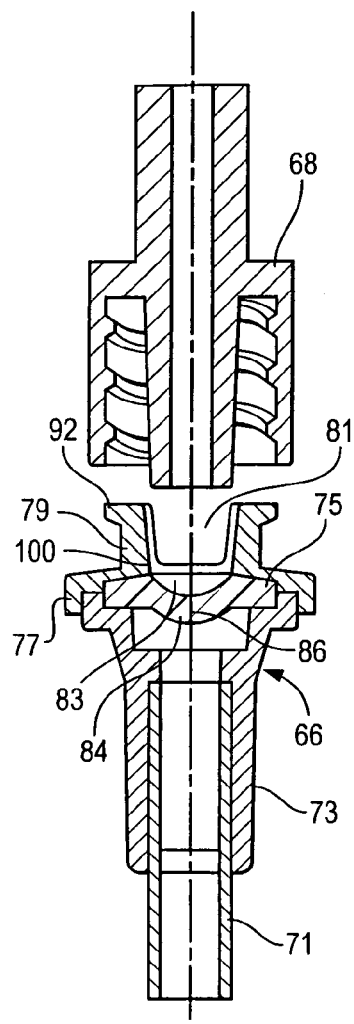
FIGS. 7-9 are longitudinal sectional views of another embodiment of an injection site and connector of this invention.
Figure 8:
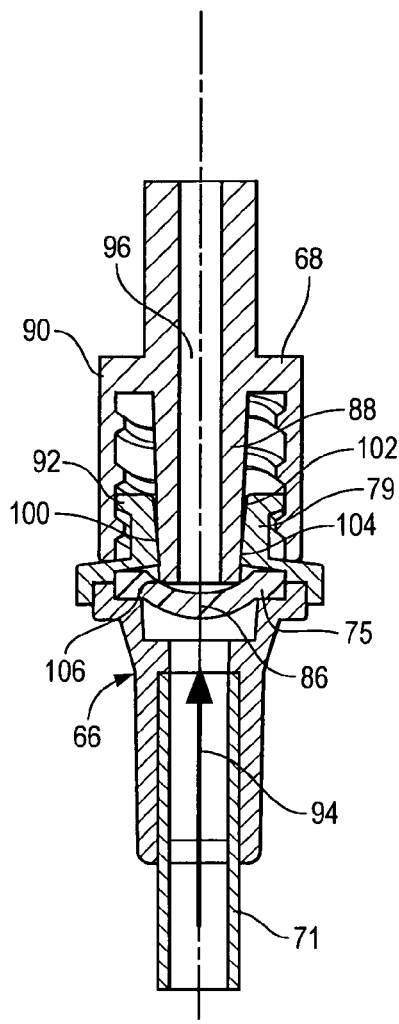
Figure 9:
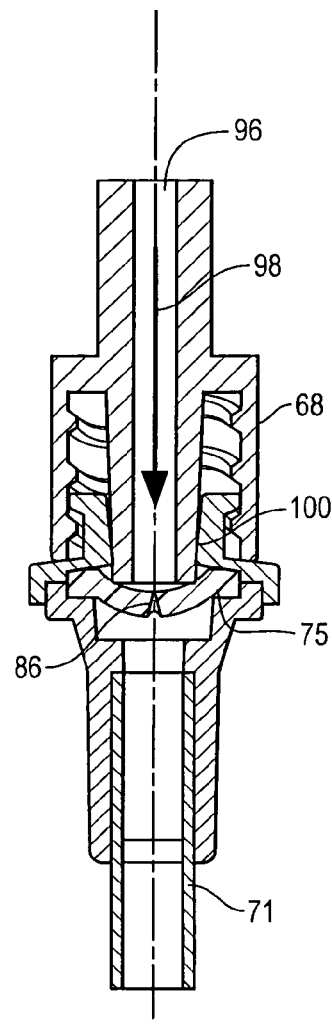

Referring to FIGS. 7-9, an injection or access site in accordance with this invention is shown, which site 66 connects with a conventional luer lock connector 68, or alternatively can connect with a luer slip connector or a sharp or blunt metal cannula, among other things. Injection site 66 is shown connected on the end of flexible tubing 71, which may be connected as part of a tubular parenteral solution or blood set, for example as a Y or T connection with the main flow path of the set. This type of valve may be beneficial for use for the administration of heparin in hemodialysis sets.

Access site 66 comprises a lower housing 73 upon which the periphery of an elastomeric wall 75 is seated, in a manner similar to previous embodiments. A cover 77 is carried on housing 73, and bonded thereto in a conventional manner. In this embodiment, retention wall 79 comprises an upstanding wall portion having a pair of diametrically opposed openings 81, one of which is shown in FIG. 7, so that a pair of conical wall sections 83 comprise retention wall 79, and define the central opening 83 that exposes the central portion of elastomeric wall 75. Elastomeric wall 75 is peripherally retained between housing 73 and cover 77 in a manner similar to previous embodiments, while the central portion of elastomeric wall 75 is exposed.

It can also be seen that the central portion 84 of elastomeric wall 75 defines a dome shape in its normal, unstretched configuration as shown in FIG. 7 (Relative to FIG. 8). The purpose of this dome shape is to suppress backflow of fluid through perforated slit 86 when the interior of housing 73 is pressurized relative to the region above slit 86. This pressure resistance can preferably be on the order of 1500 millimeters of mercury (mm. Hg), so that blood or the like will not normally bleed outwardly from injection site 66 when the set which carries it is filled with blood.

Referring to FIG. 8, the situation is shown where luer lock connector 68, commonly attached to a flexible tube of another medical fluid flow set, has engaged with injection site 66. Male luer portion 88 passes into the central opening of retention wall 79, while connector sheath portion 90 has screw threads which engage the opposed lugs 92 of retention wall 78, in a generally conventional manner. Male luer 88 advances to deform and depress elastomeric wall 75 but, in this embodiment, when male luer 88 is in its fully advanced position as shown in FIG. 8, its fully advanced position is not enough to cause slit 86 of elastomeric wall 75 to open, so that even in this situation a normal outward pressure 94 from blood pumping within injection site 66 and tube 71 is generally insufficient to cause fluid flow through slit 86 to enter into the bore 96 of male luer 88.

However, see FIG. 9, which shows the device of FIG. 8 in a similar configuration except for a change in the pressure situation 98. When pressure 98 is present in bore 96, this pressure, (such as 80-100 mm. of mercury or more) may be capable of opening slit 86 because of the geometry of elastomeric wall 74, permitting the flow of fluid through elastomeric wall 75 in the direction of arrow 98 from luer lock connector 68 into tubing 71, and from there into the fluid flow set to which it is attached. Accordingly, while fluid flow in either direction is not possible at typical pressures up to about 1500 mm Hg in the FIG. 7 situation, unidirectional fluid flow at relatively low pressure, such as at least about 80 mm Hg, is possible in the situation of FIGS. 8 and 9, because of the deflection of elastomeric wall 75 caused by engagement with male luer 88. Thus, while flow at pressures used in direction 94 is typically not possible, flow in direction 98 is readily available when desired.

FIGS. 8 and 9 utilize a connector wall 79 having a bore 100 which is of a conical shape of a different and slightly larger angle than the conical shape of male luer 88. Thus, there may be no full, annular contact between the wall of conical bore 100 and male luer 88 in area 102, (FIG. 8) while there is firm annular contact, generally with distortion of material to provide a generally releasable bond between the surfaces of bore 100 and male luer 88, in area 104. This provides an annular seal, typically less than 4 mm in axial thickness, resulting in a second seal above and beyond annular seal 106 between the tip of male luer 88 and elastomeric wall 75, and also increases the retention due to the deformation of material in the bonding area 104. This is particularly useful if a luer slip connector is used instead of luer lock connector 68, since an increase in locking retention force of the connection is provided.

Alternatively, conical bore surface 100 may receive a straight, cylindrical connector tube to provide a similar bond, with material distortion in area 104 with such tube. Alternatively, surface 100 may be cylindrical, and may engage an upper portion of a tapered connector tube to provide a similar, material-deforming bond that is spaced from the elastomeric wall.

In summary, the cracking pressure of perforation 86 is decreased by the mating of typically a luer slip or luer lock connector, the latter being shown in FIGS. 8 and 9, but the slit 86 may still be closed until a sufficient overpressure upstream 98 is applied. Blood is also prevented from passing back into a syringe attached to luer lock connector 68 by means of the blood pump pulsing of a conventional hemodialysis circuit, which may transitorily cause a downstream pressure 94 which is greater than the upstream pressure.

A purpose of the diametrically opposed openings 81 (FIG. 7) is to provide access for sterile swabbing of the top of elastomeric wall. These apertures are optional, and may be dispensed with, especially in a clinical situation where it is not intended that a connection with injection site 66 is to be made more than once. Swabbing for resterilization is usually needed only in a situation where injection site 66 is used multiple times, since, typically, it will be initially provided to the user in sterile condition.

Referring to FIG. 10, an injection site and connector 110 is shown, comprising a lower housing 112, which is closed at the top by elastomeric wall 114 having a perforated slit 116 as in previous embodiments. Elastomeric wall 114 is retained in its position in manner similar to previous embodiments, being held on annular ledge 118 of lower housing 112 by a cover 120, which acts as the retention wall, as previously discussed, and defines annular retention zone 122, which, in turn, defines central opening 124.

It can be seen that retention zone 122 defines a minimum diameter area at its bottom, next to elastomeric wall 114, with the diameter tapering outwardly as one draws farther away from elastomeric wall 114.

Luer slip (i.e. non-luer lock) connector 126 may comprise the front end of a syringe 128, or it may comprise the part of any other desired device, connected to a medical fluid flow set if desired. Luer slip 126 typically meets ISO standards.

As shown in FIG. 11, luer slip connector 126 is advanced through central opening 124, with the tapered connector 126 engaging annular retention zone 122, preferably sealingly, about the periphery of luer slip connector 126. In this embodiment, the material of retention wall 20 and retention zone 122 may be made of polycarbonate plastic, having a Rockwell hardness of about M 60, and being significantly harder than a typically polypropylene luer slip connector 126. Thus, as indicated in FIG. 11, as connection is made, the luer slip connector tube 126 is deformed by the harder material of the retention zone 122, so that the retention zone deforms or digs into the material of luer slip connector 126, thus increasing the strength of retention between the retention wall 120 and connector tube 126 and stopping the further advancement or taper luer slip connector 126 into said aperture 124. At the same time, as FIG. 11 shows, a central portion of elastomeric wall 114 is displaced and stretched by the advancing connector tube 126 to stretch open perforated slit 116, so that flow communication becomes possible between housing 112 and its connected, flexible tube 113, and syringe 128.

In this embodiment, the minimum diameter of retention zone 122 is adjusted to allow connector tube 126 to penetrate to a depth where not only does the end 130 of connector tube form a first, annular seal at 130 against the upper surface of elastomeric wall 114, but connector tube 126 can penetrate to such a depth that a second, annular side seal 132 is also formed between elastomeric wall 114 and connector tube 126, before forward motion of tube 126 is terminated by firm engagement and material deformation between tube 126 and retention zone 122.

It can be seen that the diameter of retention zone 122 can thus vary the type of connection and seal that is formed between elastomeric wall 114 and tube 126. In FIGS. 8 and 9, for example, it can be seen that the permitted depth of penetration of connector tube 88 is such that only a single, annular end seal at 106 is provided between the elastomeric wall and the connector tube 88. In the situation of FIG. 11, if the minimum diameter of retention zone 122 is a little smaller, then that same situation will take place as in FIGS. 8 and 9.

In contrast, FIG. 12 shows a connection between injection site/connector 110*a* and a conventional luer lock connector 134, which may be of ISO specification, and may be connected to a syringe 136, a tubular flow set connection, or any other desired device. As in the previous embodiment of FIGS. 7-9, tapered luer connector 138 may engage with the bore of similarly or differently tapered female retention wall locking sleeve 140, which conventionally locks with the threads 139 of luer connector 134. The bore 142 of locking sleeve 140 may be tapered at an angle slightly larger than the 6% luer taper of connector tube 138, so that, as in FIGS. 8 and 9, a lower portion 144 of bore 142 engages luer connector tube 138, with deformation of material, while at portion 146 of bore 142 the two surfaces do not deform and may even be slightly spaced. Typically, retention wall sleeve 140, as part of elastomeric wall retention cap 148, is made of harder material than luer connector tube 138, but, if desired, the converse can be true, with the deformation of material providing an annular, sealed retention zone at 144 with added resistance to separation.

In this embodiment, the minimum diameter of bore 142 is such that male luer 138 may deflect elastomeric wall 114*a* (which may be essentially identical to elastomeric wall 114 if desired) to a degree greater than the deflection illustrated in FIG. 11, opening perforated slit 116*a* more widely than in the previous embodiment and providing a deeper annular, peripheral seal 132*a* around the side of tube 138, along with the abutting annular seal 130*a* at the end of tube 138.

Thus, the depth of deflection of the connector tube and the elastomeric wall can be governed by the diameter of the retention zone 122, 144, etc. or in the case of a male luer lock connector, by the extension distance of end of tube 138 beyond end of locking skirt 134. Furthermore, the injection site/connector of this invention is very tolerant as to dimensional variation in molding, since the system has tolerance for the specific position of advancement of tube 126, 138 into connector 110, 110*a*. The situation of FIG. 2 can be created by one diameter of the retention zone; the situation of FIG. 11 created by another such diameter; and the situation of FIG. 12 can be created by a third diameter of the retention zone.

Also, the depth of penetration of tube 138 can be controlled by thickness of retention cap wall 148.

Retention wall 140 may comprise a complete sleeve, or it may carry slots in a manner similar to that shown in FIG. 7 for the purpose of permitting effective, easy swabbing of the outer surface of the elastomeric wall prior to reuse. Also, as discussed, variation in the depth of penetration by the connector tube may be controlled by adjustment of the diameter of the connector tube.

Referring to FIG. 13, injection site/connector 110*b* may be of similar design to the previous connector 110*a*. In this embodiment, a male luer lock connector 150 is shown, having a conventional, rotatable, threaded male luer locking sleeve 152, which is shown to be threadedly engaging opposed lugs 154, carried on sleeve 156, which defines an outwardly facing extension of the retention wall. Sleeve 156, in this embodiment, has no side apertures as in previous embodiments, but comprises an intact sleeve with a tapered bore which may be of slightly larger angle than the tapered outer diameter of the lower tip 158 of connector tube 160.

As in the previous embodiment, at lower bore section 144a, the material at the junction of tapered tube 158 and tapered bore 142a is deformed by engagement so that the area 144a becomes the retention zone, holding the connection together with increased force to supplement the threaded frictional retention of this system.

Additionally, without retention being controlled by rotating locking ring 152, the diameter of retention zone 144a is adjusted so that tapered tube 158 penetrates to a greater degree than in the previous embodiments, as shown, to widely open perforated slit 116b of elastomeric wall 114b, to approximate the diameter of the rest of the flow lumen as found in connected tubing 159 and bore 160 of tapered tubing 158. This embodiment is particularly useful in providing a generally laminar flow path, which is particularly desirable for the flow of blood and the avoidance of clotting. Also, it can be seen that a relatively large retention zone 144a and relatively large annular side seal 162 may be provided where the front end of tapered tube 158 passes through elastomeric wall 114b and partially through the slit.

The almost-penetrated elastomeric wall 114b serves as a transition seal and flow guide between the annular end face 163 of the connector tube 158 and the lumen wall 165 of the adjacent bore of connector 110b. In typical male/female connector sets, the flow path defines an annular "step" between the connector tube and the adjacent bore of the female connector, creating significant turbulence and pressure loss, dependent on the size of annular end face 163. By this invention, such a "step" is largely avoided, thus reducing turbulence and pressure loss. Nevertheless, tapered tube 158 still does not penetrate slit 116b but merely is in contact with the outer wall of elastomeric wall 114b because the material 169 defining slit 116b has been deformed outwardly toward the inner side wall of connector 110b.

Each of the embodiments of FIGS. 10-13 may either carry a retention sleeve such as sleeve 140 in FIGS. 12 and 156 in FIG. 13, or such a sleeve may be eliminated as in the embodiment of FIGS. 10 and 11, while still retaining the significant and improved retention of the connection because of the deformation of material achieved in the connection.

Figure 14:
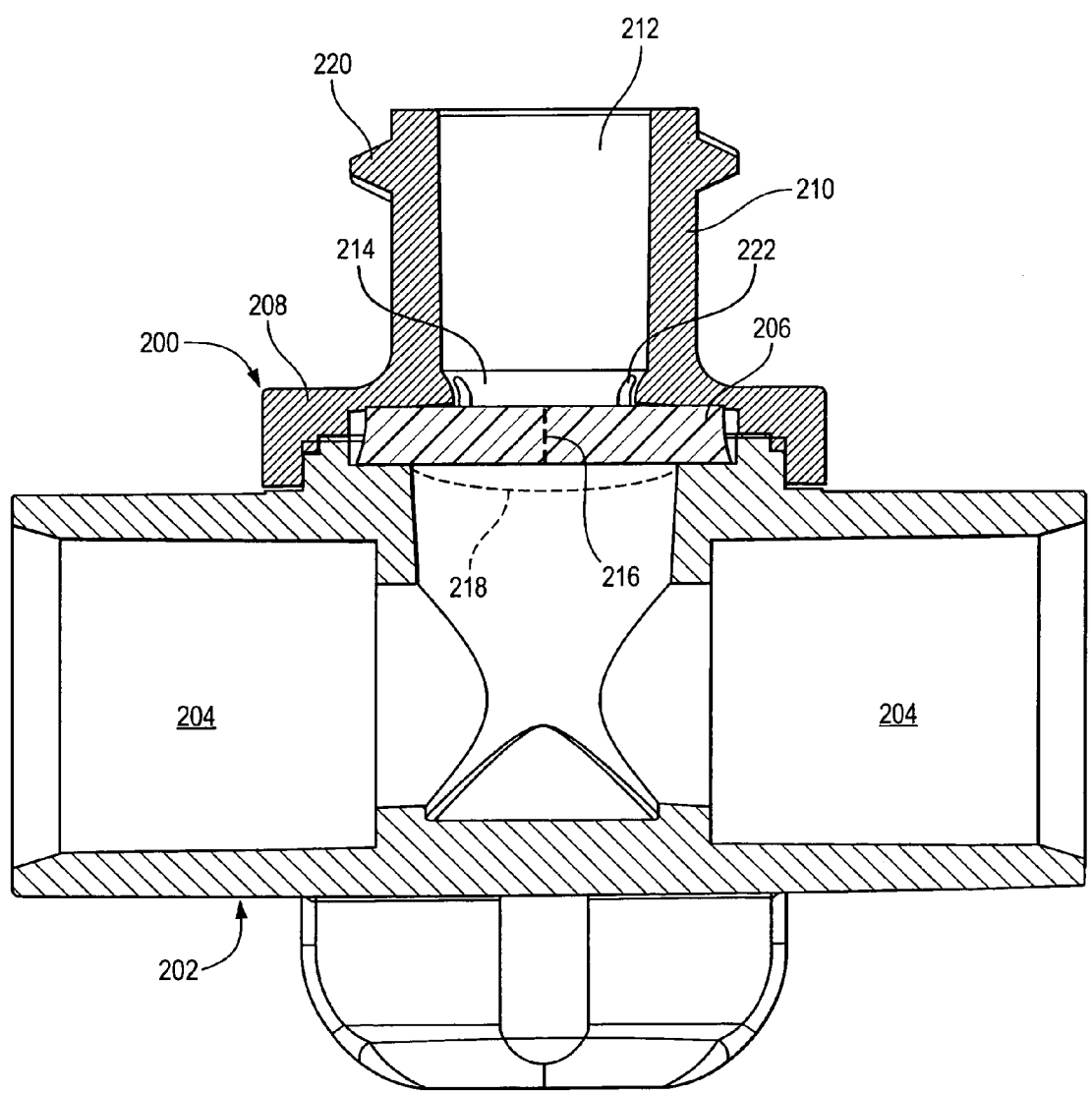
FIG. 14 is a longitudinal sectional view of another embodiment of the injection site of this invention, adapted for connection with flexible tubing of a medical fluid flow set.

Referring to FIG. 14, an injection site 200 is disclosed, being generally similar in structure and function to previous embodiments, for example, the embodiment of FIG. 6, except as otherwise shown and described herein, except that the male luer lock connector which would be used to make connection is not specifically shown in FIG. 14.

Injection site housing 202 has a pair of receptacles 204 for lengths of flexible tubing, to incorporate injection site 200 into a conventional medical set. Elastomeric wall 206 may be similar to previous counterparts, being retained on housing 202 by retention wall 208 by a conventional adhesive process, heat, or ultrasonic welding.

Retention wall 208 further comprises an outwardly facing tubular socket 210, which may have a generally cylindrical bore 212 as shown, or an inwardly tapered bore if desired, communicating with elastomeric wall 206. As shown, the tubular socket 210 of retention wall 208 defines an integral ring 214 projecting inwardly from socket tube 210, which ring defines the retention zone for sealing, material-distorting contact with a connector tube entering into bore 212, and typically pressing against and deflecting elastomeric wall 206 to open slit perforation 216. This deflection is illustrated by dotted line 218. Specifically, an ISO standard male luer may be used, with the retention zone on ring 214 being very shallow in its depth, typically on the order of 0.25 mm., because of the curved surface of ring 214 which brings only a small amount of the longitudinal distance of ring 214 into actual contact with the male luer or other connector tube. Nevertheless, because of the focused pressure provided by such a small area of the retention zone, material deformation can take place, typically in the connector tube with the material of retention zone 214 being harder, so that a good retention is provided between the retention zone on ring 214 and the connector tube, so that the connector tube will not pop out of its engagement until positively removed. Also, it can be seen that tube 210 has conventional ears or a screw thread 220, which can be used to lock the connector tube such as a male luer into place, when a device such as a male luer lock connector is used.

In this embodiment, very shallow "blow by" grooves 222 may optionally be provided in ring 214, so that residual antiseptic that is present in the system at the outer surface of elastomeric wall 206 will not be forced inwardly, but rather can bleed outwardly through grooves 222 as a connector tube is advanced into engagement with elastomeric wall 206. These grooves may be very shallow, preferably having a depth of only about 0.01 inch.

Generally, the remaining portions of the wall surrounding bore 212, which are spaced from the retention zone on ring 214, are also spaced from the connector tube. Such a system can be made capable of use with an ISO luer lock connector.

Referring to FIGS. 15-18, a medical valved connector 230 is shown, having an interior 232 for containment of fluids, and an opening into the interior which is closed with an elastomeric wall 234 having a perforation 236 as in previous embodiments. Retention wall 238 compresses the periphery of elastomeric wall 234 against annular seat 241 for securance, in a manner similar to previous embodiments.

Retention wall 238 also comprises an outwardly extending socket tube 242 which has a bore 244 communicating with a central portion of elastomeric wall 234, and conventional locking lugs 245.

A syringe 235 is provided, terminating in an ISO male luer lock connector 238, with the luer 240 of said connector 238 being in physical, annular sealing contact with a shallow retention zone 246 between the male luer 240 and the wall surrounding an inner portion of bore 244, for retention between luer 240 and the inner bore portion at zone 246, so that an annular seal is formed.

Figure 18:
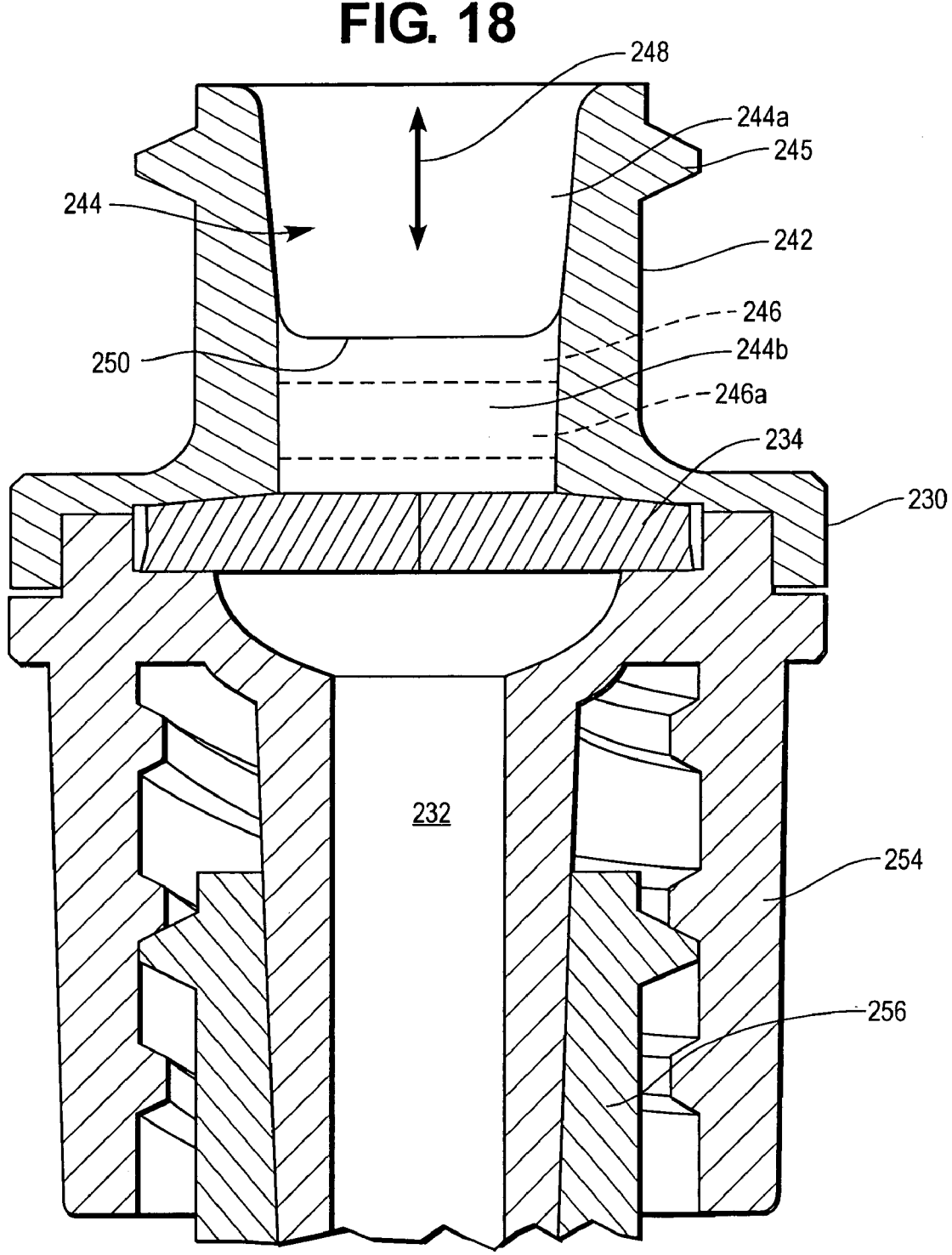
FIG. 18 is an enlarged, longitudinal sectional view of the injection site of FIGS. 15-17.

Referring to FIG. 18, an enlarged view of valved connector 230 is shown. Particularly, it can be seen that the bore 244 of socket tube 242 defines an outer, frustoconical bore portion 244a and an inner bore portion 244b, with the wall angle of inner portion 244b being less than the wall angle of outer portion 244a. As specifically shown, the wall angle of bore portion 244a is 3° from the longitudinal axis 248, while the wall angle of bore portion 244b is 0.5° to the same axis. Alternatively, inner bore portion 244b could be cylindrical if desired or counter bored, i.e. tapered in the opposite direction.

Accordingly, when a male luer 240, having a conical taper of its outer wall of essentially 1.72 degrees to axis 248, enters into bore 244a, the bore is proportioned so that male luer 240 fits loosely until it passes into inner bore portion 244b. Since the 1.72 degree taper angle of the male luer 240 is greater than the half degree taper angle of the wall of inner bore portion 244b, the wall of the male luer expands faster at a given level as it advances past the junction 250 between the inner and outer bore portions 244*a*, 244*b*. Generally, the first point of sealing contact between male luer 240 and the bore will take place at junction line 250 as the male luer advances. It may be that the tip portion of the male luer is smaller than the diameter of bore 244 at junction 250, but as the luer advances, its increasing diameter will engage the plastic material of socket 242 to form the retention zone 246. This retention zone will start with a line contact at junction 250, but, as male luer 240 is advanced, material at the retention zone 246 is deformed, and, as male luer 240 is advanced, the area of the retention zone, the seal, and the deformed material increases, since the wall angle of bore portion 244*b* is less than the outer wall angle of male luer 240.

In the outer bore portion 244*a*, the wall angle is greater than the outer wall angle of male luer 240, so sealing contact does not occur. Thus retention zone 246 will be of relatively little area extending only along a portion of the length of bore 244. Thus greater pressures per square mm. are achieved than for example in a conventional luer connection, so that deformation takes place. An adjustability of the distance of penetration of luer 240 is possible, until the locking sleeve 239 of luer lock connector 238 abuts against retention wall 238, (FIG. 17) as described also in previous embodiments, as a means to control the maximum limit of extension of male luer 240 so that it does not penetrate into or through open perforation 236, in preferred embodiments.

Figure 15:
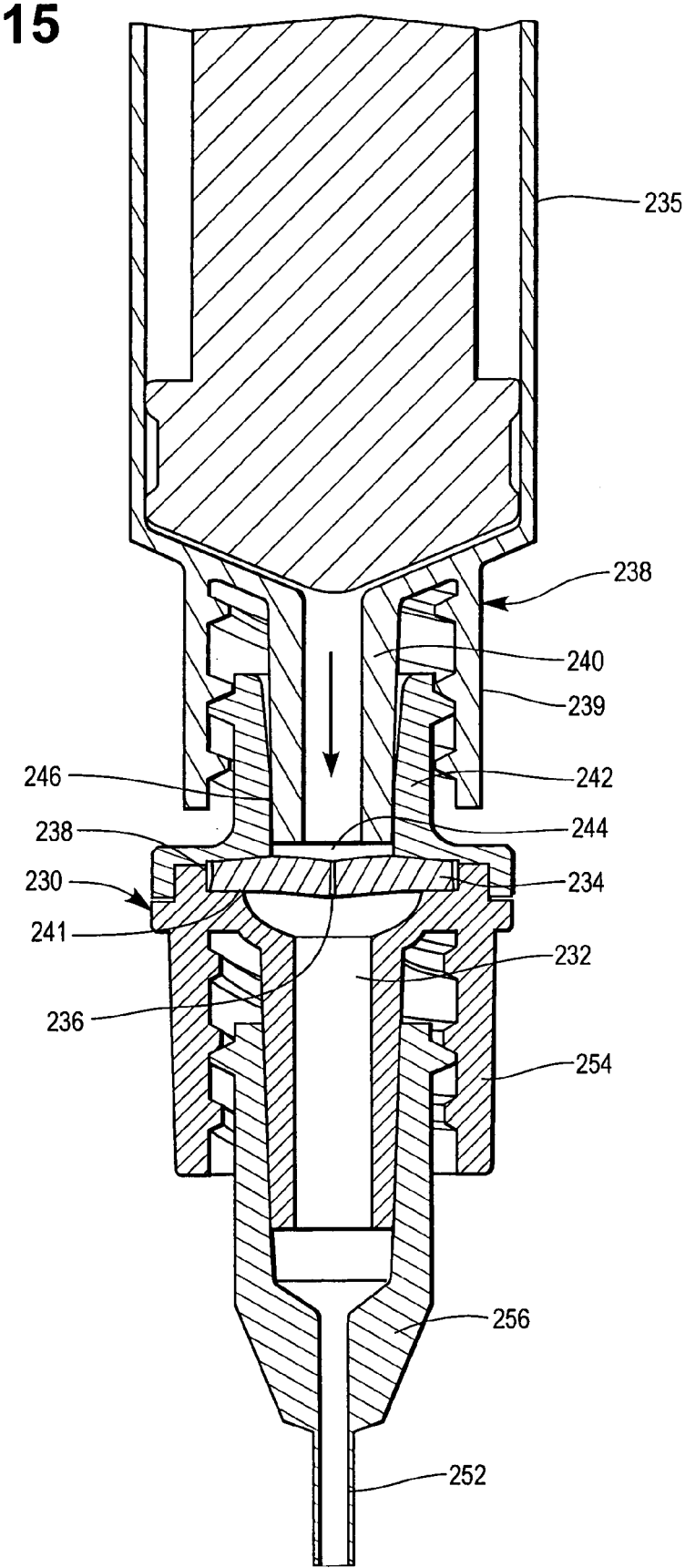
FIGS. 15, 16 and 17 are longitudinal, sectional views of another embodiment of the injection site of this invention, comprising a luer lock connector mated to a catheter locking hub, each drawing showing a different situation of use.
Figure 16:
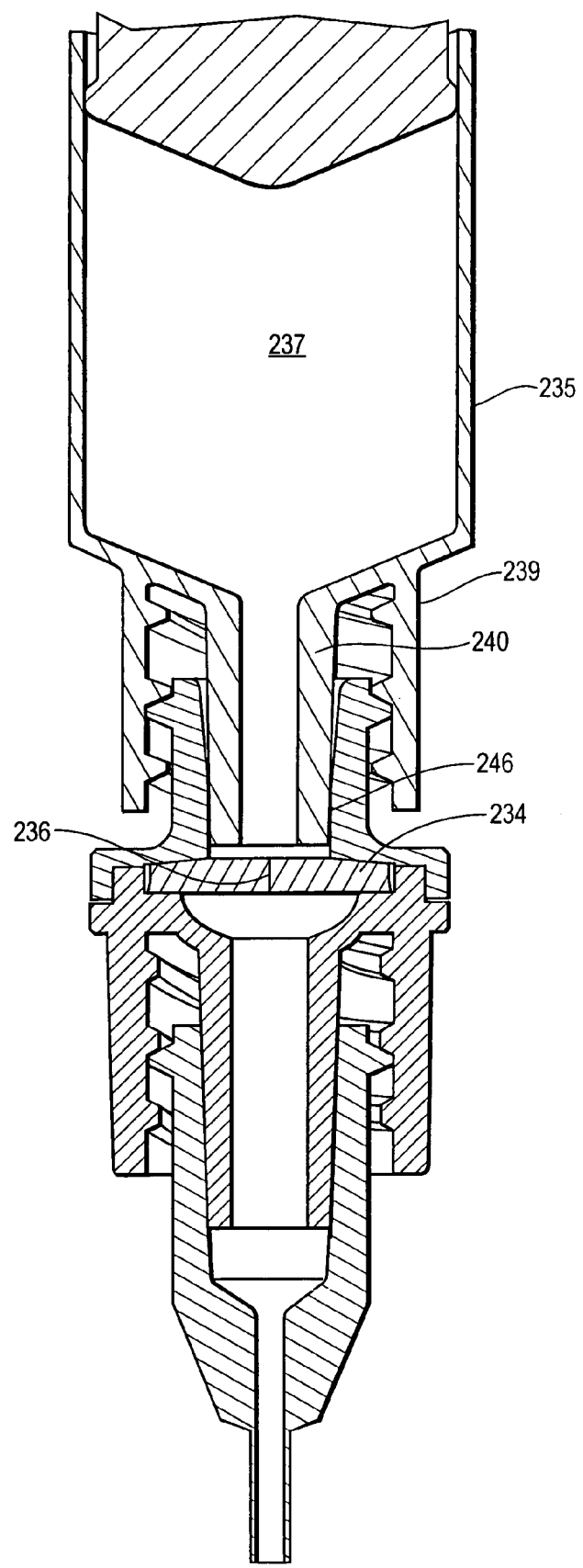
Figure 17:
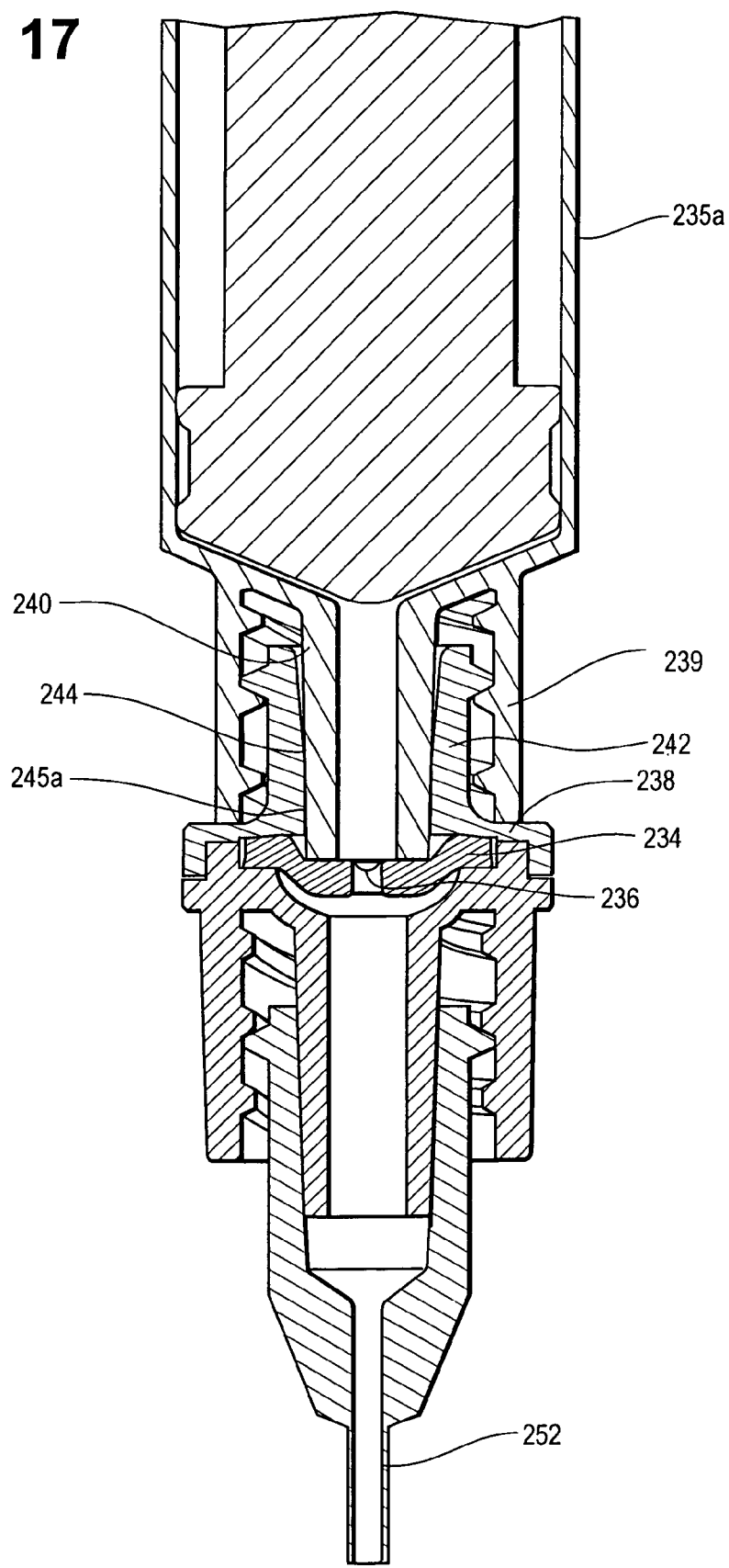

Accordingly, since male luer 240 can engage and seal with socket 242 with a variety of positions of advancement, the advantages described above can be achieved, particularly with reference to FIGS. 15-17.

In FIG. 15 (see also FIG. 18), male luer 240 is only partially advanced into socket 242, but advanced sufficiently so that an end portion of luer 242 enters into inner bore portion 244*b* and a relatively narrow retention zone 246 is formed. In this configuration, as shown in FIG. 15, when syringe 235 is pressed, fluid pressure alone can partly depress elastomeric wall 234 and open perforation 236, for transfer of fluid into chamber 232 and a connected catheter 252, which is shown to be conventionally connected to chamber 232 by another male luer lock connector structure 254 and a conventional hub 256 carried on catheter 252.

In FIG. 16, when the pressure of syringe 235 is not applied, perforation 236 is closed by the natural resilience of elastomeric wall 234.

Actually, FIG. 16 may also show the situation prior to administration of fluid by syringe 236, and FIG. 15 may illustrate the situation during such administration.

In FIG. 17, syringe 235 or another syringe 235*a*, may be further advanced into socket 242 to the full extent of advance, in which male luer 240 extends completely through bore 244, to form an enlarged retention zone 246*a* (FIG. 18), where a portion of tapered male luer 240 engages and is typically deformed by the harder material of socket 242, to form a desired, annular seal at retention zone 246*a*. In the configuration of FIG. 17, perforation 236 is forced open, and large volumes of solution may be applied without the resistance to flow that would be found in the configuration of FIG. 15. Also, IV solutions may be applied in this manner utilizing a male luer slip or luer lock connector attached to an IV set, for low pressure application of solution or blood to catheter 252, typically using gravity.

Then, if desired, syringe 235*a* may be withdrawn to the configuration of FIG. 16, closing the system and preventing fluid flow through it, and maintaining a double seal, one at the closed perforation 236 and one at the retention zone 246.

It may be needed to fill catheter 252 with heparin solution, when it is an indwelling catheter that remains in contact with the blood system of a patient. As previously described, when a catheter is so filled with heparin or other antithrombogenic agent for "locking" of the catheter, the configuration of FIG. 17 has a disadvantage, in that withdrawal of luer 240 permits elastomeric wall 234 to naturally and resiliently withdraw to the configuration of FIG. 16. This, in turn, causes a suction to be generated in the interior of catheter 252, which, at its other end, can suck blood into the distal tip of the catheter. This is undesirable, since the blood can be stagnant there and will clot.

Accordingly, syringe 235*a* or another medical device, is withdrawn to the configuration of FIG. 16. Alternatively, syringe 235*a* may be removed, and a fresh syringe 235 with the desired heparin solution may be attached into the configuration of FIG. 16 where the tip of male luer 240 is spaced from elastomeric wall 234. Then, as shown in FIG. 15, pressure is applied by syringe 235, forcing anticoagulant solution into the lumen of catheter 252, to "lock" the catheter in an otherwise conventional manner, without as much suck back of blood into the catheter when the luer lock connector 238 is removed, as one would find in the situation of FIG. 17.

Thus, a medical valve connector is provided in which a connector tube 240 can occupy a plurality of positions while sealing is maintained, at retention zone 246, with the different positions having different advantages.

Figure 19:
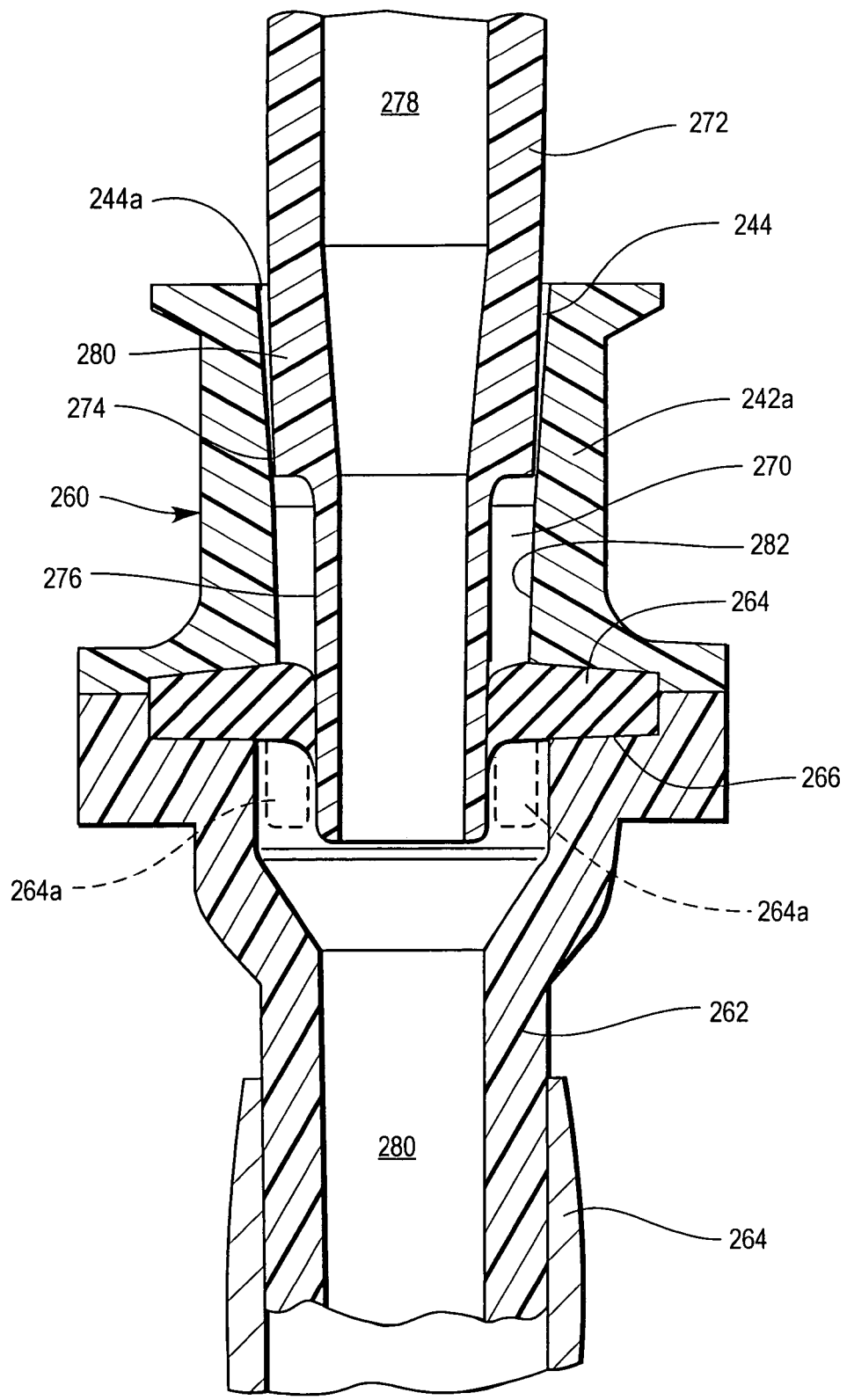
FIG. 19 is a longitudinal, sectional view of another injection site embodiment.

Referring to FIG. 19, an injection site 260 is shown which is similar in its upper portion 242*a* to the injection site of FIG. 18, but it carries a lower housing 262 which is capable of conventional sealing connection with an end of flexible tubing 264.

As in FIG. 18, an elastomeric wall 264, comprising a wall of elastomeric material, rests its peripheral area in annular seat 266. Tubular socket member 242*a* may be substantially similar in design to socket member 242. Particularly, the dimensions of bore 244 and the two different bore sections of differing angular relationship may be the same as in the embodiment of FIG. 18.

FIG. 19 shows how another design of connector tube 272 can be used to provide a sealed, annular connection zone 274, while at the same time this particular connector tube defines a typically cylindrical forward extension 276 which fully penetrates a perforation in elastomeric wall 264 to stretch and deflect elastomeric wall 264*a*, and to provide an open flow path between lumen 278 of connector tube 272 and the interior 280 of housing 262 and flexible tubing 264.

As before, outer bore portion 244*a* may have a wall angle of about 3°, while the conical section 280 of connector tube 272 may have a typical conical luer taper of essentially 1.72°, to cause binding and formation of annular retention zone 274 as connector tube 272 is advanced. This may take place with deformation of plastic at the retention zone, either the plastic of connector tube 272 or socket 242*a*, or both depending upon the hardness of the materials, to cause a significant resistance to disconnection and a solid, annular seal that prevents access to the area of bore 270 outside of extension tube 276.

Upon withdrawal of connector tube 272, elastomeric wall 264 recloses its perforation to provide sealing of the system.

Inner bore portion 282 may typically have a slightly inwardly tapering wall angle of about ½°, to form a slightly frustoconical inner surface, or it may be cylindrical.

In all embodiments, upon withdrawal of the connector tube, the elastomeric wall can typically reclose its perforated slit to provide resealing again of the interior of the injection site/connector of this invention.

The above has been offered for illustrative purposes only, and is not intended to limit the scope of the invention of this application, which is as defined in the claims below.

That which is claimed is:

1. A medical device having an interior for containment of fluids; an opening into the interior; an elastomeric wall comprising a fixedly placed, flexible barrier across said opening and having at least one closed perforation centrally positioned; and a retention wall positioned adjacent to a peripheral portion of said elastomeric wall, said retention wall defining a central opening, said retention wall having a retention zone surrounding said central opening, to engage and retain a connector tube having a length and having a leading end which is advanced into said central opening to press against and partially displace said elastomeric wall, and to open said centrally positioned perforation through said elastomeric wall, for direct flow through said perforation into said connector tube, said retention zone being made of a material of sufficient hardness that material of a minor portion of the length of an engaged and retained connector tube is deformed by engagement with the retention zone, to increase strength of retention between the retention wall and the connector tube, said retention zone being sized to engage and hold said connector tube before said leading end fully penetrates said elastomeric wall.

2. The device of claim 1 in which said retention zone comprises a ring-shaped seal.

3. The device of claim 2 in which a plurality of spaces divide said retention zone into separate sections.

4. The device of claim 2 in which said retention zone has an axial depth of no more than about 4 mm.

5. The device of claim 4 in which said retention zone has an axial depth of no more than 0.6 mm.

6. The device of claim 1 in which said retention wall comprises a tapered-bore tube extending outwardly from said elastomeric wall, said retention zone comprising a minimum diameter portion of the tapered bore of said tube.

7. The device of claim 6 in which said connector tube is engaged and retained by said retention zone, said retention wall comprising a tapered bore sleeve, said connector tube having an outward taper in the same direction as, but of a lesser angle than, said tapered-bore sleeve retention wall.

8. The device of claim 1 in which the material of the retention zone has a hardness of at least about Shore A 80.

9. The device of claim 1 in which said connector tube is engaged and retained by the retention zone in a position to engage and deflect said elastomeric wall to open a slit in said elastomeric wall without said connector tube extending through said slit.

10. The device of claim 9 in which said connector tube has a blunt tip.

11. The device of claim 1 in which said connector tube is engaged and retained by the retention zone in a position to engage and deflect said elastomeric wall, to open a slit in said elastomeric wall without said connector tube extending through said slit, said connector tube having a blunt tip, and in which said retention zone is ring-shaped and projecting inwardly from an extending sleeve.

12. The device of claim 11 in which said retention zone has an axial depth of no more than about 1 mm.

13. The device of claim 12 in which said retention wall comprises a tapered-bore tube extending outwardly from said elastomeric wall, said retention zone comprising a minimum diameter portion of the tapered bore of said tube.

14. The device of claim 13 in which said tapered-bore tube comprises at least one side opening.

15. The device of claim 12 in which said retention wall comprises a plate portion extending transversely of the axis of said retained connector tube, said plate portion defining said central opening.

16. The device of claim 12 in which the material of said retention zone has a hardness greater than the hardness of said connector tube.

17. The device of claim 1 which is connected with an ISO standard male luer connector tube.

18. A medical device having an interior for containment of fluids and an opening into the interior; an elastomeric wall having at least one closed and centrally positioned perforation and comprising a fixedly placed, flexible barrier across said opening; and a retention wall positioned adjacent to a peripheral portion of said elastomeric wall, said retention wall defining a central opening, said retention wall having a retention zone surrounding said central opening, to engage and retain a connector tube having a length and a leading end, which is advanced into said central opening to partially displace said elastomeric wall and to open said perforation through said elastomeric wall, for direct flow through said perforation into said connector tube, said retention zone having an axial depth of no more than about 4 mm, and sized to engage and hold a minor portion of the length of said connector tube before said leading end fully penetrates said elastomeric wall.

19. The device of claim 18 in which said retention zone is ring-shaped and extending inwardly from a sleeve.

20. The device of claim 19 in which said retention zone participates in a ring-shaped seal with said connector tube.

21. The device of claim 18 in which said retention zone has an axial depth of no more than 0.6 mm.

22. The device of claim 18 in which said retention wall comprises a tapered-bore tube extending outwardly from said elastomeric wall, said retention zone comprising a minimum diameter portion of the tapered bore of said tube.

23. The device of claim 22 in which said tapered-bore tube comprises at least one side opening.

24. The device of claim 18 in which said retention wall comprises a plate portion extending transversely of the axis of said retained connector tube, said plate portion defining said central opening.

25. The device of claim 18 in which the material of the retention zone has a hardness that is greater than the hardness of said connector tube.

26. The device of claim 18 which is connected with an ISO standard male luer connector tube.

27. The device of claim 26 in which said connector tube comprises an ISO standard male luer of a luer lock connector.

28. The device of claim 25 in which said axial depth is no more than about 1 mm.

29. The device of claim 18 in which said connector tube engages said elastomeric wall to form a first annular seal between the connector tube end and the elastomeric wall, and a second annular seal between the side of the connector tube and the elastomeric wall.

30. The device of claim 1 in which the increase of said strength of retention between the retention wall and the connector tube comprises at least 100 grams.

31. The device of claim 1 in which said connector tube engages said elastomeric wall to form a first annular seal between the connector tube end and the elastomeric wall, and a second annular seal between the side of the connector tube and the elastomeric wall.

32. The device of claim 1 in which said retention zone is spaced from the elastomeric wall.

33. The device of claim 1 in which the closed perforation does not extend completely through said elastomeric wall.

34. The device of claim 33 in which said perforation has an end that is adjacent to a rupturable plastic coating skin layer on said elastomeric wall.

35. A tubular connector system, which comprises:
a connector tube having a conically tapered outer wall having an angle, and a socket tube having a tubular, frustoconical bore portion for receiving the connector tube and retaining said connector tube by engagement with said bore portion, the frustoconical bore portion having a first bore portion with a first wall angle that is less than the conical taper angle of said connector tube, and a second bore portion of said frustoconical bore portion having a second wall angle that is greater than the conical taper angle of said connector tube, said engagement between said connector tube and said bore portion extending along only a small portion of said connector tube and bore portion.

36. The connector system of claim 35 in which the conical taper angle of the connector tube and the wall angle of the first bore portion of the frustoconical bore portion together define a difference in said angles of about 1.2°.

37. The connector system of claim 35 in which the second bore portion of said frustoconical bore portion having the wall angle greater than the conical taper angle of the connector tube is an outer portion of said frustoconical bore portion.

38. The connector system of claim 18 in which said elastomeric wall is free of added lubricant.

39. The connector system of claim 1 in which said elastomeric wall is free of added lubricant.

40. The device of claim 1 wherein the open perforation defines an opening, the connector tube defines a tube internal bore for fluid flow through the connector tube and through the open slit, and the perforation opening is sized in accordance with the connector tube internal bore.

41. The device of claim 40 wherein the elastomeric wall surrounding the open perforation provides a smooth transition to the interior opening.

42. The device of claim 40 wherein the perforation opening and connector tube internal bore are sized to minimize turbulence and pressure loss thereacross.

43. The device of claim 40 wherein the retention wall and elastomeric wall permit insertion of the connector tube to a depth to deform the elastomeric wall and open the perforation such that turbulence and pressure loss through flow path therealong is minimized.

44. The device of claim 40 wherein flow of fluid through the connector tube and the open perforation is generally laminar.

* * * * *